US006387617B1

(12) United States Patent
Asher et al.

(10) Patent No.: US 6,387,617 B1
(45) Date of Patent: May 14, 2002

(54) CATALYTIC NUCLEIC ACID AND METHODS OF USE

(75) Inventors: Nathan Asher, Bet-Shemesh; Yaron Tikochinsky, Jerusalem, both of (IL); Andy Ellington, Bloomington, IN (US)

(73) Assignee: Intelligene Ltd., Jerusalem (IL)

( * ) Notice: Subject to any disclaimer, the term of this patent is extended or adjusted under 35 U.S.C. 154(b) by 0 days.

(21) Appl. No.: 09/257,503

(22) Filed: Feb. 25, 1999

Related U.S. Application Data

(63) Continuation-in-part of application No. PCT/IL97/00282, filed on Aug. 26, 1997.

(30) Foreign Application Priority Data

Aug. 26, 1996 (IL) ................................................ 119135
Mar. 17, 1997 (IL) ................................................ 120466

(51) Int. Cl.$^7$ ........................ C07H 21/00; C07H 21/02; C12P 19/34; C12Q 1/68
(52) U.S. Cl. ........................ 435/6; 435/91.21; 435/91.3; 435/91.31; 536/23.1; 536/25.1
(58) Field of Search .......................... 435/6, 91.1, 91.2, 435/91.21, 91.3, 91.31; 514/44; 536/23.1, 24.3, 24.31, 24.32, 24.5, 25.1, 25.3, 25.4

(56) References Cited

U.S. PATENT DOCUMENTS 5,472,840 A   12/1995   Stefano .......................... 435/6

FOREIGN PATENT DOCUMENTS

| EP | 0754483 | 1/1997 |
| WO | 9413791 | 6/1994 |
| WO | 9413833 | 6/1994 |
| WO | 9617086 | 6/1996 |
| WO | 9627026 | 9/1996 |

OTHER PUBLICATIONS

Gewirtz et al. Facilitating oligonucleotide delivery: Helping antisense deliver on its pomise. Proc. Natl. Acad. Sci. USA 93 (1996), 3161–3163.*

Michels et al. Conversion of a group II intron into a new multiple–turnover ribozyme that selectively cleaves oligonucleotides: Elucidation of a reaction mechanism and structure/function relationships. Biochem. 34 (1995), 2965–2977.*
Lehman et al. Evolution in vitro of an RNA enzyme with altered metal dependence. Nature 361 (1993), 182–185.*
Rojanasakul, Y. Antisense oligonucleotide therapeutics: Drug delivery and targeting. Adv. Drug Delivery Rev. 18 (1996), 115–131.*
Stromberg et al. 2'–amino–2'–deoxyguanosine is a cofactor for self–splicing in goup I catalytic RNA Biochem. Biophys. Res. Com. 183 (1992), 842–848.*
Stull et al. Antigene, ribozyme and aptamer nucleic acid drugs: Progresss and prospects. 12 (1995), 465–483.*
Robertson et al., "Selection in vitro of an RNA enzyme that specifically cleaves single–stranded DNA" *Letters to Nature*, vol. 344, pp. 467–468, (1990).
Porta et al., "An Allosteric Hammerhead Ribozyme", *Bio/Technology*, vol. 13, pp. 161–165, (1996).
Bartel et al., "Isolation of New Ribozymes from a Large Pool of Random Sequences", *Science*, vol. 261, pp. 1411–1418, (1993).
Abdallah, et al., Non–viral gene transfer: Applications in development biology and gene therapy, Bio. Cell, 1995, 1–7, 85.
Somia, et al., Generation of targeted retroviral vectors by using single–chain variable fragment: An approach to in vivo gene gelivery, Proc. Natl. Acad. Sci. U.S.A., 1995, 7570–7574, 92.

* cited by examiner

*Primary Examiner*—Sean McGarry
*Assistant Examiner*—Thomas G Larson
(74) *Attorney, Agent, or Firm*—Browdy and Neimark

(57) ABSTRACT

A nucleic acid molecule is provided which is initially catalytically inactive but which can complex with a specific co-factor, e.g., a nucleic acid molecule or a non-nucleic acid molecule, to form a catalytically active nucleic acid molecule. The catalytically active nucleic acid molecule can be used to detect the presence of a non-nucleic acid co-factor or of a nucleic acid co-factor using the nucleic acid sequence of the present invention.

14 Claims, 31 Drawing Sheets

5) (a)
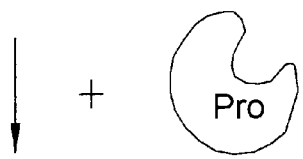
+ Mg$^{++}$
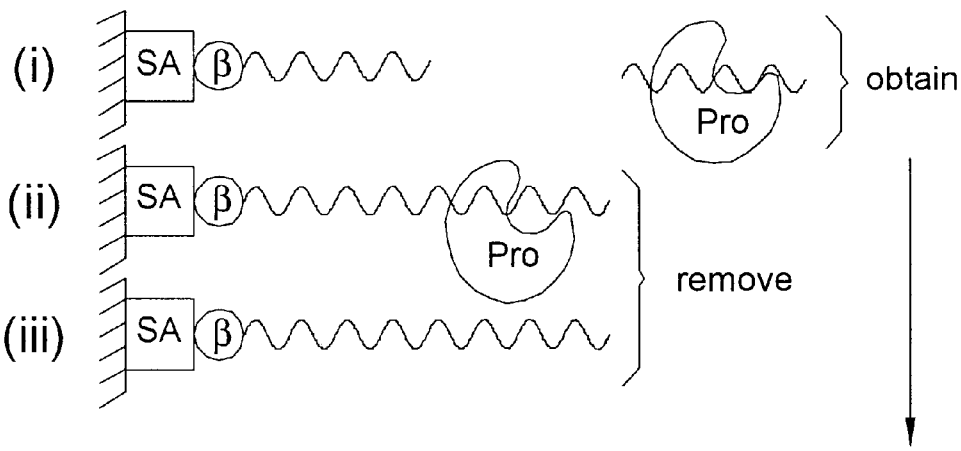
6) PCR
FIG. 1 continue

```
                    G
                 A     U
                  C:G
                  U:A
                  C:G
                  U:A
                 C   C
                 A   A
                 A   |
                 A   A
                  G:U
                  G:C
                  G:C
                  G:C
                  C:G      UAAAU      A
5'--GAAAA-UCUGCC-UAA-- A:U---GC        CAGC A
        ::::::              ::       :::: |
       AGAUGG               CG       GUCG U
     |         C         C   UAAAU      A
     |           A         U
     |             C         A
  U-CUCAAC          AUCAGCA
 A  ::::::          :::::  :
    A-GAGUUG--AAGGUA--UAGUC-U-A-AA----C
                                       U
     SNYP94C                           G
     ‾‾‾‾‾‾‾                           C        G-GAUC--3'
                                                A
                                                C
                                   GGAGAAUG     G
                                          A:U
                                          U:A
                                          G:C
                                    P1P94  G  A
                                    ‾‾‾‾‾  U  G
```

FIG. 4C

```
                        G
                      A   U
                      C:G
                      U:A
                      C:G
                      U:A
                      C   C
                      A   A
                      A   |
                      A   A
                      G:U
                      G:C
                      G:C
                      G:C
                      C:G        UAAAU        A
5'--GAAAA-UCUGCC-UAA--  A:U---GC         CAGC A
       ::::::              ::         :::: |
       AGAUGG              CG         GUCG U
   |       C            C   UAAAU        A
   |         A        U
   |          C      A
U-CUCAAC           AUCAGCA
A  ::::::          ::::: :
   A-GAGUUG--AAGGUA--UAGUC-U-A-AA----C
                                     U
    SNYP96                           G
                                     C            G-GAUC--3'
                                     A           A
                                     U           C
                                                 G
                                                 U
                              GGAGAAUG        A
                                     G:C
                              P1P96   G   A
                                      U   G
```

FIG. 4D

Km = 4.7 μM
Kcat = 6.min-1

```
                    C
                  A   U
                  C:G
                  U:A
                  C:G
                  U:A
                  C   C
                  A   A
                  A   |
                  A   A
                  G:U
                  G:C
                  G:C                    Fragment A
                  G:C
                  C:G       UUAAU     AAUA-3'
5'--GAAAA-CGCCCA-UAA-- A:U---AC        CACC
         ::::::           ::          ::::
         GCGGGU           UG          GUGG-5'
    |       U           U   CGAUC
    |        A           A
    |         U           A              Fragment B
3' AUGGAAAU           UUAGGCU
   ::::::             :::::: :
5' -ACCUUUA--AAGGUA--AAUCC-A-AP9.0C:G-GAUC--3'
                              U:A
                              G:C         Fragment C
                              C:G
                              A:U
                              U:A
                              G:C
                              G   A
                              U   G
```

FIG. 17

```
         U   C
       U       G
         C - G
         A - U
  PPP    G - C
   HO    U   A
         C   G
         A   U
         C   G
         A   U
         C   G
         G   C
[tag]    A   UCGUG-N90-CUCGUGAUGUCCAGUCGC 3'
                         GAGCACTACAGGTCAGCG 5'
```

CATALYTIC NUCLEIC ACID AND METHODS OF USE

This application is a continuation-in-part of copending parent application Ser. No. PCT/IL97/00282, filed Aug. 26, 1997.

FIELD OF THE INVENTION

The present invention concerns molecules and methods for detection of specific agents in a medium.

BACKGROUND OF THE INVENTION

Ribozymes are typically RNA molecules which have enzyme-like catalytic activities usually associated with cleavage, splicing or ligation of nucleic acid sequences. The typical substrates for ribozymes catalytic activities are RNA molecules, although ribozymes may catalyze reactions in which DNA molecules (or maybe even proteins) serve as substrates.

Ribozymes which are active intracellularly work in cis, catalyzing only a single turnover, and are usually self-modified during the reaction. However, ribozymes can be engineered to act in trans, in a truly catalytic manner, with a turnover greater than one and without being self-modified. Two distinct regions can be identified in a ribozyme: the binding region which gives the ribozyme its specificity through hybridization to a specific nucleic acid sequence (and possibly also to specific proteins), and a catalytic region which gives the ribozyme the activity of cleavage, ligation or splicing.

It has recently been proposed to use ribozymes in order to treat diseases or genetic disorders by cleaving a target RNA, such as viral RNA or messenger RNA transcribed from genes that should be turned off. This was proposed as an alternative to blockage of the RNA transcript by the use of antisense sequences. Owing to the catalytic nature of the ribozyme, a single ribozyme molecule cleaves many molecules of target RNA and therefore therapeutic activity is achieved in relatively lower concentrations than those required in an antisense treatment (WO 96/23569).

The use of ribozymes for diagnostic purposes has been only seldomly mentioned. WO 94/13833 describes a method for detecting nucleic acid molecules in a solution by tailoring a specific ribozyme molecule having two regions, one complementary to the nucleic acid sequence to be detected, and the other complementary to a co-target molecule bearing a detectable label. The ribozyme is able to specifically and reversibly bind both to a selected target nucleic acid sequence and to the labeled co-target. When both the target and the co-target are bound, the ribozyme undergoes a conformational change which renders it active and able to cleave the label of the co-target, and the free label can then be detected. Upon cleavage of the co-target, the ribozyme is able to re-associate with an additional co-target, cleaving more label and producing more detectable signals.

WO 94/13791 concerns a regulatable ribozyme molecule which upon binding to a ligand alters its activity on a target RNA sequence. Again, as in WO 94/13833, binding to the target causes a conformational change in the ribozymes which renders it active. An example for such a change, is in the presence in the ribozyme of a redundant sequence which masks the core region of the ribozyme. Only upon binding of the target sequence to said redundant sequence, the core becomes unmasked, and thus active.

U.S. Pat. No. 5,472,840 (Stefano, J. E.) discloses a nucleic acid sequence comprising the MDV-1 motif (capable of autocatalytic replication in the presence of the enzyme of the Q-beta replicase) which becomes active only when it forms a specific structure, comprising the sequence GAAA, with a target nucleic acid molecule. The ribozyme of Stefano is prepared by modifying an existing ribozyme and features only the activity of cleavage in the presence of a very restricted range of target molecules.

Lizardi, M. P. and Helena Porta (*Biotechnology* 13:161–164 (1995)) disclose an allosteric hammerhead ribozyme that is a priori inactive, and is triggered by specific interaction with a DNA allosteric effector that is complementary to a single-stranded loop in the RNA stranded ribozyme. This publication discloses a ribozyme which becomes active when a part of which becomes double-stranded.

The above publications disclose ribozymes which become catalytically active, either due to a conformational change or due to a hybridization reaction which render them double-stranded. These types of reactions may also occur spontaneously, for example, if a ribozyme is inactive due to the presence of a redundant sequence which masks its core region, this redundant sequence may either break, or open, even in the absence of the target, and thus the ribozyme will become catalytically active even without a target. Spontaneous reversion to an active state, of course renders the ribozymes impractical for diagnostic purposes.

Israel Patent Applications 112799 and 115772 (corresponding to PCT/US96/02380) disclose methods for the detection of catalytically active ribozymes in a medium, wherein typically the catalytically active ribozyme is used as a reporter for the presence of other biomolecules in a test sample. In accordance with the methods disclosed in these applications, catalytically active ribozyme, if present in an assayed medium, yields a reaction cascade in which more catalytically active ribozymes are produced in a positive-feedback manner in one of various embodiments specified in these applications. The catalytically active ribozyme may be produced, or activated only in the presence of an assayed molecule.

GENERAL DESCRIPTION OF THE INVENTION

In the following, the term "nucleozyme" will be used to denote an oligonucleotide or a complex formed between an oligonucleotide and a nucleic acid sequence or between an oligonucleotide and another molecule e.g. an oligonucleotide, a protein or a polypeptide, etc., which possesses a catalytic activity. An example of a nucleozyme is a ribozyme.

The term "proto-nucleozyme" will be used to denote a nucleic acid molecule or a complex of two or more such molecules, which has a priori no catalytic activity but which becomes catalytically active upon formation of a complex with a co-factor. A proto-nucleozyme is in fact a nucleozyme with a missing component, which missing component is completed by the co-factor. The complex between the proto-nucleozyme and the co-factor may also at times be referred to as "catalytic complex" and is in fact a nucleozyme since it has catalytic activity. The proto-nucleozyme may consist of deoxynucleotides (dNTP's), ribo-nucleotides (rNTP's), as well as other nucleotides such as 2'-O-methyl nucleotides, or any combinations of these.

The term "catalytic activity" is meant to encompass all possible catalytic activities of nucleozymes, including cleavage, ligation, splicing-out (cleaving both ends of a short nucleic acid sequence to remove it from a longer sequence and ligating the ends of the cut), splicing-in (cleaving open a nucleic acid sequence, inserting another short nucleic acid sequence and ligating the ends of the cut), rearrangement, as well as additional catalytic activities such as phosphorylation, kinase like activity, addition or removal of other chemical moieties, biotinilation, gap filling of missing nucleotides, polymerization, etc.

The term "co-factor" will be used to denote a molecule or a moiety within a molecule (e.g. a certain DNA sequence within a larger DNA molecule), which complexes with the proto-nucleozyme to yield a catalytic complex, namely an active nucleozyme. The co-factor completes a missing portion of the proto-nucleozyme so that it can become catalytically active, and turn into a nucleozyme.

The present invention relates to novel proto-nucleozymes and their use. The proto-nucleozymes of the invention have substantially no catalytic activity, as they miss a critical component, which is essential for the catalytic activity, said missing component is completed by the co-factor. In other words, in order to become catalytically active, the proto-nucleozymes need to complex with the co-factor, so as to form a catalytic complex (the nucleozyme) which can exert a catalytic activity. The term "having substantially no catalytic activity" is meant to denote that the proto-nucleozyme possesses either no catalytic activity or possesses a catalytic activity which is very much lower (typically by several orders of magnitude) than that of the catalytic complex.

As pointed out above, there are known ribozymes which complex with a factor (termed also target), e.g. a protein or another nucleic acid sequence which causes the ribozymes to undergo conformational change whereby the catalytic activity of the ribozyme becomes more pronounced. However, in distinction from such prior art ribozymes, the proto-nucleozyme of the invention, a priori misses an essential component and said co-factor provides said missing component. Examples of such missing components are sequences in the core region of the nucleozyme. The co-factor may be a protein which fills a gap between two ends of nucleic acid strands of the nucleozyme or which joins such two ends; or may be a nucleic acid sequence capable of binding between two free ends of the proto-nucleozyme thus filling a gap.

Given the structural an functional features of the proto-nucleozyme, when in solution, it does not have the capability of spontaneously converting into a catalytically active form, since its activation is not dependent solely on a conformational change which may occur spontaneously but rather on completion of a missing component. This feature is a further distinction from prior art inactive ribozymes, which have the capability to spontaneously undergo confor-mational change, albeit at a low rate, and exert some catalytic activity even in the absence of a co-factor. Thus, unlike prior art inactive ribozymes, such as those described above in the Background of the Invention section of this specification, when the ribozymes of the invention are used, there is substantially no background activity in the absence of the co-factor. For example, when proto-nucleozymes of the invention are used in diagnosis, there is essentially no "noise", namely, there is a very high signal-to-noise ratio and there are virtually no false-positive results. By another example, when used in therapeutics, the proto-nucleozymes of the invention, will exert a very high target specificity and only in the presence of an appropriate target, the catalytic complex (the nucleozyme) will be formed and exert its activity.

The proto-nucleozymes of the invention can be prepared both by in vitro evolution, in a manner to be described below, or by means of rational design by nucleic acid synthesis, for example, by using a sequence of a known ribozyme and leaving a gap of several missing nucleotides in its core region.

The present invention provides a proto-nucleozyme, which is a nucleic acid molecule or a complex of nucleic acid molecules, which have essentially no catalytic activity but which can complex with a co-factor to form a nucleozyme which possesses a catalytic activity. The proto-nucleozyme lacks a component essential for the catalytic activity of the nucleozyme and said co-factor provides said component.

The component which is missing in the proto-nucleozyme and which is provided by the co-factor for conversion of the proto-nucleozyme into a catalytically active nucleozyme may be a missing nucleic acid segment of one or more nucleotides (hereinafter "gap") or a missing bond between two nucleotides (hereinafter "nick"), etc. The co-factor may thus be a nucleic acid segment which can bridge the gap or nick. For this purpose, such a co-factor nucleic acid segment has sequences which can hybridize with complementary sequences in the two strands on both sides of the gap or nick and in the case of a gap, may comprise also the missing sequence. It should be noted that at times the co-factor segment may hybridize to and provide a bridge between two nucleic acid stretches of the proto-nucleozyme other than those immediately flanking the gap or nick. In addition, the co-factor may also at times be a macromolecule such as a protein, an oligosaccharide, etc., which can complex with the two nucleic acid terminals flanking the gap or nick and accordingly bring to bridging of the two. The gap or nick may be between two different oligonucleotide strands which are functionally joined together by said co-factor or may be between ends of the same oligonucleotide wherein the co-factor in such yields the function of a functional closed oligonucleotide loop.

Such proto-nucleozymes may be obtained ("engineered") by means of in vitro evolution or by means of rational design.

The specific co-factor may be any molecule which can chemically interact with nucleotides in any manner, e.g. by the formation of hydrogen bond, by electrostatic bonds, by Van der Waals' interactions, etc. Such molecules include, proteins, peptides, oligopeptides, antibiotics, phosphate nucleotides such as ATP, GTT, cyclic AMP, and others, carbohydrates, lipids, nucleic acid sequences (DNA or RNA sequences), etc.

At times it may be desired to modify the proto-nucleozyme in order to increase its nuclease resistance, which may be achieved by replacing some of the natural nucleotides, by non-natural nucleotides such as 2'-O-methyl nucleotides (Usman et al., *Nucleic Acids Symposium Series*, 31:163–164, 1994).

A currently preferred, but not exclusive, use of the proto-nucleozymes of the invention is as a diagnostic tool for the detection of the presence of a certain agent in a medium. For this purpose, a proto-nucleozyme will be designed such that said agent will be the specific co-factor. When said agent will be present in the tested medium, a catalytic complex will form and the catalytic activity, which will then be assayed, will then serve as a gauge for the presence of said agent in the medium.

By one option the agent may be a disease identifying agent and may be the nucleic acid sequence or an amino acid sequence identifying the disease, for example, identifying an infectious agent or a genetic disease. By another option the agent may be the result of a nucleic acid amplification technique, for example, nucleic acids amplified by PCR, 3SR, NASBA and the like.

For this preferred embodiment, it is preferred to use proto-nucleozymes which possess absolutely no or ummeasurable catalytic activity, and the catalytic activity is essentially manifested then only upon the formation of the catalytic complex. In such case, there will be an essentially zero background signal and a detection of a catalytic activity will then be an unequivocable ("all or none") indication of the presence of said agent (which is the specific co-factor) in the medium. Where a proto-nucleozyme is used which possesses some small catalytic activity, the level of the catalytic activity will have to be determined in order to assay the presence of said agent in the medium.

The present invention further provides a method for the detection of an agent in a medium, which comprises the following steps:

(a) contacting said medium with a proto-nucleozyme, wherein said agent is the specific co-factor required for the formation of a catalytic complex;

(b) providing or maintaining conditions allowing catalytic activity of the catalytic complex; and (c) assaying for the presence of products of the catalytic activity in the medium, such presence indicating the presence of said agent in the medium.

An example of the type of catalytic activity which may be determined in step (c) above, is cleavage of nucleic acid sequence. For example, the catalytic complex may cleave, from an immobilized nucleic acid substrate, a small fragment bearing a detectable label. Then, detection of a free label in the reaction medium is indicative of the activity of the catalytic complex, which is in turn an indication of the presence of the assayed agent in the medium.

Other examples of catalytic activity which can be determined in step (c) are ligation, splicing out, splicing in, etc. All the above three catalytic activities result in a change in the distance between two sequences of nucleotides which are the substrates for the reaction. In ligation and splicing out two sequences are brought together and in splicing two sequences are spaced apart. One of these sequences may bear, for example, a fluorescent containing moiety (e.g. rhodamine), and the other sequence may bear a fluorescent quenching (e.g. fluorescein) containing moiety or a fluorescent enhancing moiety; the change in the distance between the two sequences may then be determined by measuring the change in fluorescence emission, which is quenched (in the case of a fluorescent quencher) or enhanced (in the case of a fluorescent enhancer) when the two sequences are adjacent one another, and enhanced or quenched, res, when the two sequences are spaced apart.

One preferred method for assaying for the products of the catalytic activity is by means of the self amplifying ribozyme cascade reaction disclosed in International Application PCT/US96/02380 and corresponding Israel Patent Applications 112799 and 115772, the contents of which are being incorporated herein by reference. Briefly, the catalytic complex (or the nucleozyme) once formed catalyzes a reaction which brings to activation of a priori inactive nucleozymes (identified in the above-referenced applications as ribozymes), and those catalytically active nucleozymes then act catalytically to activate additional ribozymes and so forth, in a self amplifying positive feedback reaction cascade. This amplified signal thus serves as a gauge for the presence of the initial catalytically active nucleozyme in the medium; the presence of such an initial catalytically active nucleozyme is in turn an indication of the presence of the specific co-factor which is the agent to be detected and which complexes with the proto-nucleozymes to yield the catalytic complex of the initial ribozyme in the medium.

The unique capability of the proto-nucleozymes to become catalytically active in the presence of a specific co-factor, makes them useful also as therapeutic agents in certain targeted therapies. In some diseases, disease-bearing cells differ from normal cells in expression of certain expression products. This is the case, for example, in viral diseases where diseased cells differ from other cells by the fact that they express viral proteins. The proto-nucleozyme may be engineered so that upon complexation with a viral-specific protein, (which will be the specific co-factor), it will have a certain cytotoxic catalytic activity or its catalytic activity will yield a cytotoxic reaction product. The catalytic activity may be targeted at a specific nucleic acid sequence or a gene expression product such that the undesired gene expression (e.g. of a viral origin or of a cellular origin) will be inhibited. For example, the catalytic activity may cleave the sequence of an undesired MRNA, thus inhibiting production of an undesired protein. Such proto-nucleozymes may be provided in formulations allowing their entry into the cell, e.g. a liposome formulation, and while the proto-nucleozymes will enter many cells, they will assume their catalytic activity and will thus destroy only the desired cell population for example, or inhibit the expression of undesired genes only in the viruses bearing cells.

In addition to viral diseases, there are also other diseases where diseased cell express or contain products which are not found in normal cells or found in the latter cells in only small amounts. Such is the case, for example, in cancer; in a variety of infectious diseases other than viral diseases; in various genetic diseases where diseased cells in diseased individuals contain a mutant gene and abnormal expression products; etc.

Accordingly, the present invention provides a method for selectively destroying a specific cell population, containing or expressing a specific agent, the method comprising:

(a) providing a proto-nucleozyme of a nucleozyme, which nucleozyme has a catalytic activity which is cytotoxic to the cell or has cytotoxic reaction products, and wherein said agent is a specific co-factor to said proto-nucleozyme;

(b) inserting said proto-nucleozyme to cells containing or expressing said agent, or applying said proto-nucleozymes to tissue, suspected of containing a population of cells containing or expressing said agent, under conditions or using a vehicle, so as to insert said proto-nucleozyme to said cells.

In the case where the proto-nucleozyme is intended for destroying viral-containing cells, the co-factor may, for example, be a viral-associated protein, e.g. in the case of HIV, the HRV-TAT protein.

The cytotoxicity of the nucleozyme may be manifested in a variety of ways. For example, a nucleozyme, once becoming active, may catalyze a reaction yielding formation of cytotoxic reaction products. Such cytotoxic reaction products may, for example, be reaction production which competitively inhibit one or more essential metabolic or catabolic pathways in the cells. By another example, the catalytic activity of the cytotoxic ribozyme may by itself yield breakdown of substances which are produced within the cells or transported into the cell through the cells' membranes, which are essential for the cells' growth and survival. Other examples may be nucleozymes which degrade mRNA, either in general or such having specific sequences, nucleozymes which breakdown tRNAs, nucleozymes which degrade a variety of proteins, and others.

The present invention also provides a method for inhibiting expression of undesired genes in cells, comprising:

(a) providing a proto-nucleozyme of a nucleozyme, which nucleozyme has a catalytic activity which is targeted at a specific nucleic acid sequence or gene expression product so that once active within a cell, the undesired gene expression will be inhibited;

(b) inserting said proto-nucleozyme to cells containing or expressing said gene, or applying said proto-nucleozyme to tissues suspected of having a population of cells containing or expressing said gene, under conditions or using a vehicle so as to insert said proto-nucleozyme to said cells.

By an embodiment of this latter aspect, the co-factor of the proto-nucleozyme is either a nucleic acid sequence of such gene, or a transcription or expression product of the gene.

The inhibition of the DNA expression by this latter method may, for example, by breakdown of the specific mRNA, breakdown of an expression product of the gene, or breaking down regulatory substances regulating expression of the gene.

The above methods where said proto-nucleozyme is inserted into cells, may be useful in human therapy. The proto-nucleozymes within the framework of such therapies may be administered in vivo or may be contacted with cells ex vivo, which cells are then inserted back into the body.

According to its therapeutic aspect, the present invention further provides a pharmaceutical composition e.g. for use in destroying a specific cell population, which comprises said proto-nucleozyme and a pharmaceutically acceptable carrier. The carrier will preferably be of a kind which allows insertion of the proto-nucleozyme into cells, e.g. a liposome carrier or any other carrier known in the art.

As explained above, the nucleozyme of the invention may be produced by rational design or by way of in vitro evolution.

As will be explained further below, in vitro evolution does not require any decision in advance on the exact mechanism of formation of the catalytic complex between the proto-nucleozyme and the specific co-factor. The exact mechanism of activation evolves during such in vitro evolution.

The term "in vitro evolution", refers to a method of generating and selecting nucleic acid sequences (which may be DNA or RNA sequences, or sequences comprising both dNTP's and rNTP's comprising naturally or non-naturally occurring nucleotides) having desired characteristics, without a priori knowing the exact construct of the selected nucleic acid sequence. Typically, it entails production of a huge number of random, or partially random, nucleic acid sequences or complexes comprising one or more nucleic acid sequences, then providing the conditions required for selection of those sequences which feature a specific property (for example, adding a protein and selecting only those nucleic acid sequences which show a catalytic activity only in the presence of the protein). The selected nucleic acid sequences are then amplified, for example, by polymerase chain reaction (PCR), and then selection and amplification steps are repeated over many cycles, e.g. ranging from 10 to 100, resulting in an enrichment of the reaction mixture by those nucleic acid sequences or complexes which feature the desired property. It is at times useful to progressively increase the threshold criteria for selection in each round of a selection and amplification. For example, as the steps of the in vitro evolution proceeds, only species having progressively higher affinity to the desired protein are selected.

In vitro selection methodologies to probe RNA function and structures are summarized in a review by Conrad, R. C., *Molecular Diversity* 1:69–78 (1995) and have been studied in models for autocatalytic replication of RNA by Giver et al. (G. R. Fleischaker et al. (Editor), *Self-Production of Supramolecular Structures* 137–146, (1994), Klewer Academic Publishers).

The present invention thus provides an in vitro evolution method for the production of a proto-nucleozyme of the invention which upon formation of a catalytic complex with a specific co-factor manifests a specific catalytic activity which is either absent or considerably lower in the proto-nucleozyme. The method which has both positive and negative selection steps, comprises:

(a) preparing a panel of different nucleic acid molecules, at least part of the sequence in the molecules of the panel is a random or a partially random sequence, such that said part has a different sequence in different molecules of the panel;

(b) adding said co-factor to said panel and incubating under conditions permitting said catalytic activity;

(c) separating between the nucleic acid molecule of said panel which feature said catalytic activity and such which do not, to obtain a first selected panel of nucleic acid molecules which feature said catalytic activity;

(d) amplifying the nucleic acid molecules of said first selected panel;

(e) incubating said first selected panel with a reaction mixture, being devoid of said co-factor, under conditions permitting said catalytic activity;

(f) removing nucleic acid molecules which featured catalytic activity, thereby obtaining a second selected panel of nucleic acid molecules devoid of the removed nucleic acid molecules; and (g) repeating steps (b)–(f) over a plurality of cycles, e.g. about 10–100 cycles, to obtain said proto-nucleozyme.

By one embodiment, the molecules in the panel are comprised of an entirely random sequence with the exception of two short flanking sequences for attachment of the PCR primers. By another embodiment of the invention the molecules in the panel are constructed based on a known nucleozyme sequence. For example, the molecule may be comprised of a constant, ribozyme-derived sequence attached to a random or semi-random sequence. Generally, a random sequence may be prepared, for example, by utilizing a nucleic acid synthesizer.

In the above method, positive selection steps (steps (b)–(d)) precede the negative selection steps (steps (e)–(f)), this being a preferred embodiment of the invention. However, it is possible also to perform the method in a reverse sequence, namely, first the negative selection steps and then the positive selection steps.

Another example is a panel of molecules, all based, on a known ribozyme sequence, and wherein the nucleotides in the entire molecule or in a part thereof have a certain probability (e.g. 70–99%) of being identical to the known sequence. Such a semi-random sequence means that each nucleotide has a certain probability of being different than the corresponding nucleotide in the original ribozyme (e.g. this probability is 30–1%, respectively). The preparation of the panel begins with a known nucleozyme sequence and then semi-random sequences are created based thereon by replacing some of the nucleotides with the different, random, nucleotides ("doping"). The level of doping is typically about 1–30%. The doping may also be performed in each cycle or once in several cycles, thereby slowly bringing to the evolution of a proto-nucleozyme with a high specificity towards the specific co-factor.

An example of how such selection is made, can be drawn from the specific case where the catalytic activity is cleavaged in cis. Initially, all members of the panel may be immobilized on a solid support. Those sequences which possess the catalytic activity of cis cleavage in the positive selection steps i.e. in the presence of the specific co-factor (steps (b)–(d)) are freed to the reaction mixture and are collected and amplified, for example using PCR. After amplification, the collected sequences are allowed to cleave in the absence of the specific co-factor, and those freed in the negative selection steps (steps (e)–(f)), are removed.

In the steps of selection, it is at times desired to apply the exact conditions in which the proto-nucleozyme will eventually be used. Where the proto-nucleozyme is intended for use within the framework of a diagnostic assay, the conditions of selection will typically be similar to those in the diagnostic assay. For example, where the co-factor is a blood protein, and the proto-nucleozyme is intended for use in a diagnostic assay for detection of such a protein in the blood, the selection (both positive and negative) may be carried out in a reaction medium mimicking the conditions (both the chemical environment and the temperature) which will exist in the assay, e.g. blood-like composition and room temperature.

In the following, a preferred in vitro evolution method, useful for the preparation of proto-nucleozymes of the invention, will be described. It should however be noted that this in vitro evolution method is an example, and the invention is not limited to the preparation of proto-nucleozymes to this specifically described method, neither to in vitro evolution preparation methods in general.

A Preferred in Vitro Evolution Method

A major problem in an in vitro evolution method for the preparation of a proto-nucleozyme having the above defined features, is the difficulty in separating between candidates of proto-nucleozymes which feature catalytic activity only in the presence of the specific co-factor, and those which feature the specific catalytic activity both in the presence of said co-factor as well as in its absence, or in the presence of other agents. In other words, there is difficulty in eliminating the undesired candidates.

Many times, especially in the initial cycles of the in vitro evolution, there are molecules which feature catalytic activity also in the absence of the specific co-factor (which molecules should be removed), but do so at a very low efficiency; thus the negative selection step in which such molecules are removed, may require extremely prolonged incubation times, rendering impractical the whole process of in vitro evolution (which requires multiple cycles of negative selection steps). Under standard incubation times only a small percentage of the molecules which are slow acting but feature a catalytic activity also in the absence of the co-factor, but which should be removed in the negative selection steps, will actually feature the catalytic activity in the given incubation time. This can result in incomplete removal of undesired molecules in the negative selection step, and may eventually lead to false positive results when the proto-nucleozymes are used for diagnosis. In principle, the molecules removed during the negative selection step may be collected, and may be used to "fish out", by hybridization, other identical molecules of the same species of proto-nucleozymes candidates which should have been removed, but due to the short incubation time did not have a chance to feature the catalytic activity. However, the sequences of candidate proto-nucleozymes which feature catalytic activity both in the presence of the specific co-factor and in the presence of other agents, (to be removed), and the sequences of the candidate proto-nucleozymes which feature the desired property only in the presence of said co-factor (to be maintained), may be very similar (the difference in the sequence of the two may be very small relative to the large size of the candidate proto-nucleozyme) so that it would be practically impossible to distinguish between the two by hybridization.

The solution to this problem is the addition of a random tag sequence to each of the candidate proto-nucleozyme in the initial oligonucleotide mixture comprising a panel of different candiproto-nucleozymes, so that after amplification, all oligonucleotides of the same species (i.e.

all molecules amplified from an original parent molecule) have the same random tag sequence. This tag sequence, does not form a part of the functional sequence of the nucleozyme (i.e. the tag is a redundant sequence). The functional sequence is the part that when the proto-nucleozyme reacts with the co-factor which is the part which imparts the catalytic activity. The tag sequence is linked to a variable sequence (candidate for evolving to the functional sequence). While the variable sequence of different oligonucleotide species may be similar (for example since all variable sequences were "doped" from an original known sequence of a ribozyme); the tag sequence is completely different from one oligonucleotide species to the other.

Thus, when, following a negative selection step, oligonucleotides featuring catalytic activity in the absence of said co-factor are collected in order to be removed, it is then possible to first cleave the cleavable sequence, and thus to collect separately only the tag sequences of the undesired oligonucleotides. These tag sequences, which are random, have a very high probability of being different in each species of oligonucleotide molecules, and thus may be used to effectively "fish out" complementary tag sequences of other members of the undesired oligonucleotide species to be removed and are thus capable of discovering "latent" oligonucleotides which, if the incubation time was long enough, would have featured catalytic activity even in the absence of the co-factor. Since the "fishing out" i.e. elimination process is based only on the hybridization of the unique tag sequence (which is different than the tag sequences of the other species), the fact that the variable sequence of the oligonucleotides which are to be removed is very similar to the variable sequence of the oligonucleotides which should be maintained, does not interfere with the selection process.

Thus, the in vitro evolution method for obtaining proto-nucleozyme of the invention, which together with a co-factor form a catalytic complex having a catalytic activity imparted by a functional sequence of said proto-nucleozyme, comprises:

(a) preparing a mixture of different oligonucleotide candidates for evolving to said proto-nucleozymes each of which comprises a variable sequence being a candidate for evolving into said functional sequence and a tag sequence, each of the two sequences being different than corresponding sequences of different oligonucleotides in the mixture, the variable sequence and the tag sequence being linked by at least one cleavable sequence;

(b) processing the mixture through positive and negative selection steps, each step optionally followed by an oligonucleotide amplification step, there being at least one positive selection step and at least one negative selection step, these steps comprising:

(ba) a positive selection step comprising applying said specific co-factor and separating. between the oligonucleotides which have and those which do not have catalytic activity to obtain a first selected mixture comprising a first group of oligonucleotides featuring catalytic activity in the presence of the co-factor;

(bb) amplifying said first group of oligonucleotides in said first selected mixture to produce a plurality of copies of each of said first group of oligo-nucleotides to obtain a first amplified mixture;

(bc) a negative selection step comprising:

(bca) applying a reaction mixture devoid of the specific co-factor and separating between a second group of oligonucleotides which do not have catalytic activity in the absence of the co-factor and a third group of oligonucleotides having the catalytic activity in the absence of the co-factor, to obtain a second selected mixture comprising said second group of oligonucleotides and a third selected mixture comprising said third group of oligonucleotides;

(bcb) amplifying said third group of oligonucleotides in said third selected mixture to produce a plurality of copies of each of said third group of oligonucleotides to obtain a second amplified mixture;

(bcc) cleaving the cleavable sequence of the oligonucleotides in the second amplified mixture, separating between the variable and the tag sequences and collecting the tag sequences;

(bcd) contacting the collected tag sequences with the second selected mixture under stringent conditions of hybridization and removing hybridized oligonucleotides from other oligonucleotides of the second mixture, thereby obtaining a fourth selected mixture of oligonucleotides essentially devoid of oligonucleotides which have catalytic activity in the absence of the co-factor;

where said positive selection step precedes said negative selection step, said positive selection step is applied on said mixture prepared in step (a) and said negative selection step is applied on said first amplified mixture; and where said negative selection step precedes said positive selection step, said negative selection step is applied on said mixture obtained in step (a) and said positive selection step is applied on said fourth mixture.

Preferably, the positive selection step should precede the negative selection step. It is preferable that in the positive selection step of each consecutive cycles the conditions become more and more stringent, for example, shorter assay times, harsher sample preparation conditions etc.; while in the negative selection step conditions become less and less stringent, allowing even those oligonucleotides with a very small catalytic activity in the absence of the co-factor, to exert their catalytic activity (and thus to be removed) for example by utilizing longer incubation times, etc.

Where the negative selection step is repeated a plurality of times, each step or several steps may be performed in the presence of another agent which is not the co-factor. For example, where the co-factor is a certain protein, each step in the negative selection may be incubated in the presence in the medium of another non-co-factor protein being present in a different negative selection step.

It should be noted that by the above in vitro evolution method, proto-nucleozymes which are converted into nucleozymes by mere conformational change are eliminated. Such proto-nucleozymes can convert into a catalytically active form (i.e. into the nucleozyme) even spontaneously, without the co-factor, albeit at a low probability. Due to the unique and highly sensitive negative selection step employed in the above in vitro evolution method, all such proto-nucleozymes are identified and are removed, retaining only those proto-nucleozymes which have essentially no catalytic activity and need the co-factor, which complete the missing component, to become catalytically active.

The present invention will now be illustrated in the following non-limiting examples with an occasional reference to the annexed drawings:

BRIEF DESCRIPTION OF THE DRAWINGS

FIGS. 4C and 4D show various modifications of the SunY ribozyme SNYP94C (SEQ ID No:24), P1P94 (SEQ ID NO:25), P1P96 (SEQ NO:26), and SNYP96 (SEQ ID NO:27);

FIG. 17 shows SunY construct in which fragment B (indicated in bold letters in the text) was replaced by 16s rRNA sequence of chlamydia in which Fragment A is SEQ ID NO:33, Fragment B is SEQ ID NO:34, a and Fragment C is SEQ ID NO:35;

FIG. 22 shows a schematic representation of an RNA sequence pool which undergoes selection by in vitro evolution (SEQ ID NO:37–38);

Figure 3A:
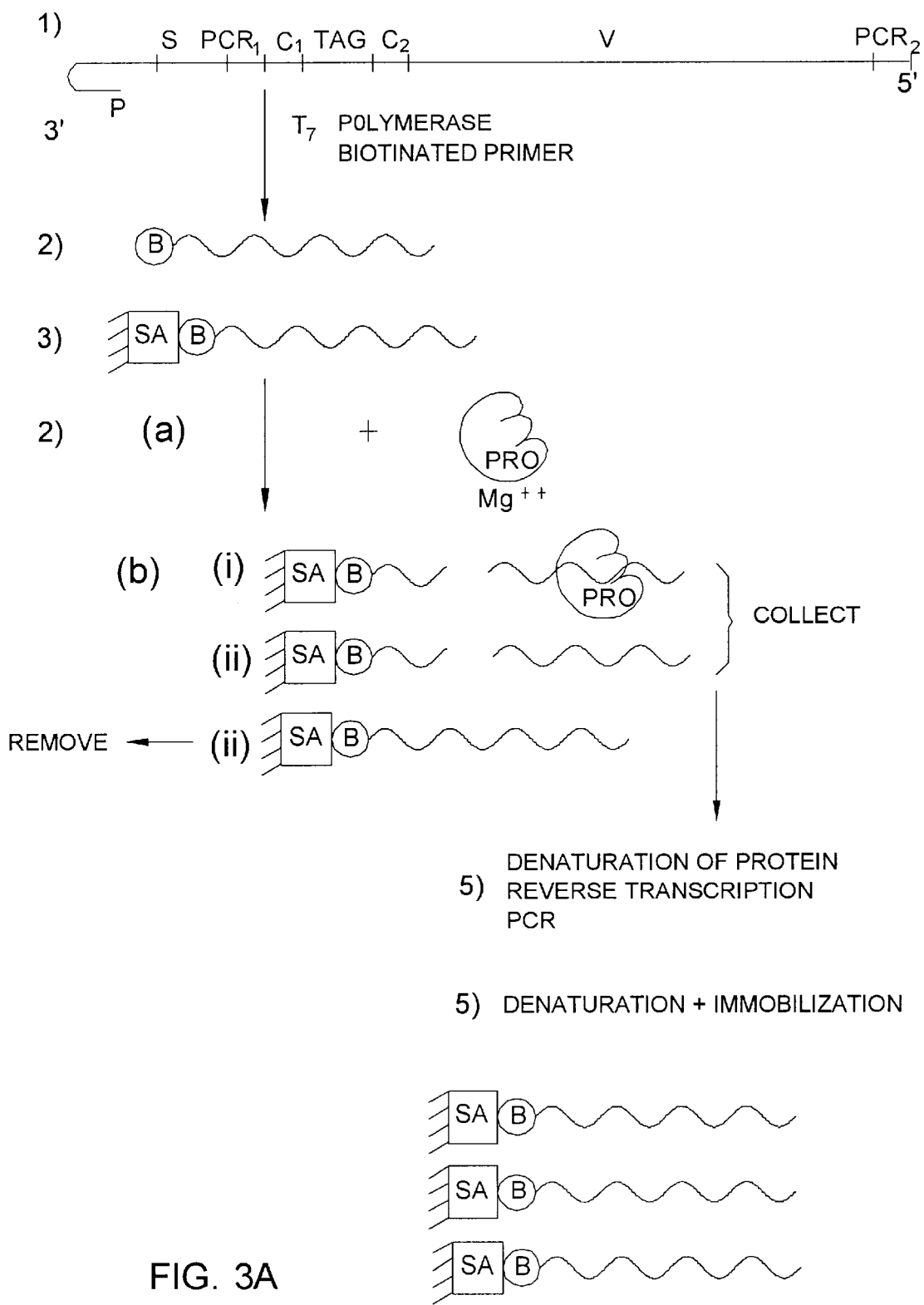
FIG. 3 shows an improvement in the negative selection step of the method of FIG. 1.
Figure 3B:
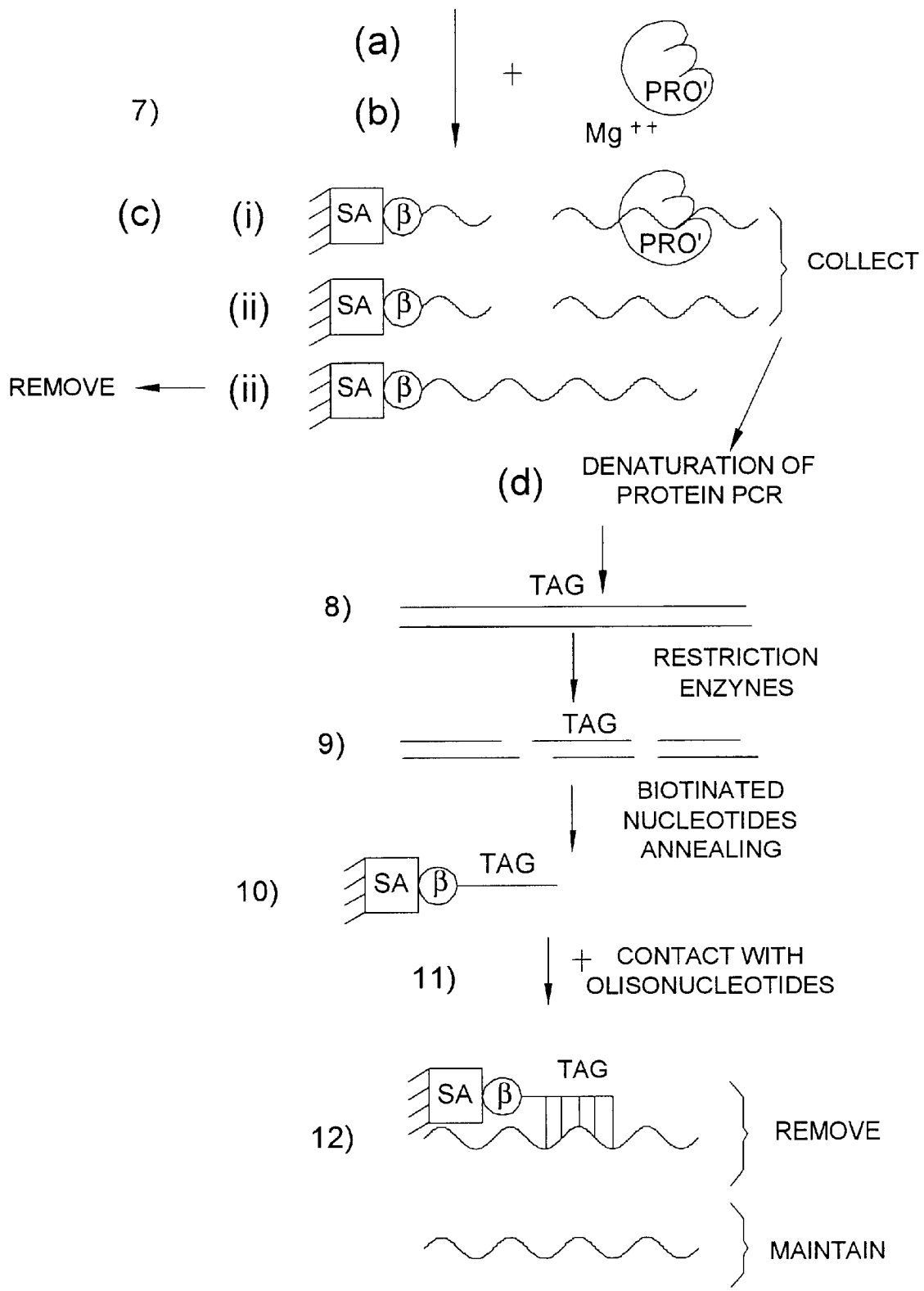

In the description the following terms and definitions will be used:

Group I intron—An intron having a three-dimensional structure as depicted in FIG. 3A and a conserved nucleotide structure and secondary structure depicted in FIG. 3B.

6.2-a substrate for SunY ligation having the sequence: 5' CCCUCU 3'.

Figure 4A:
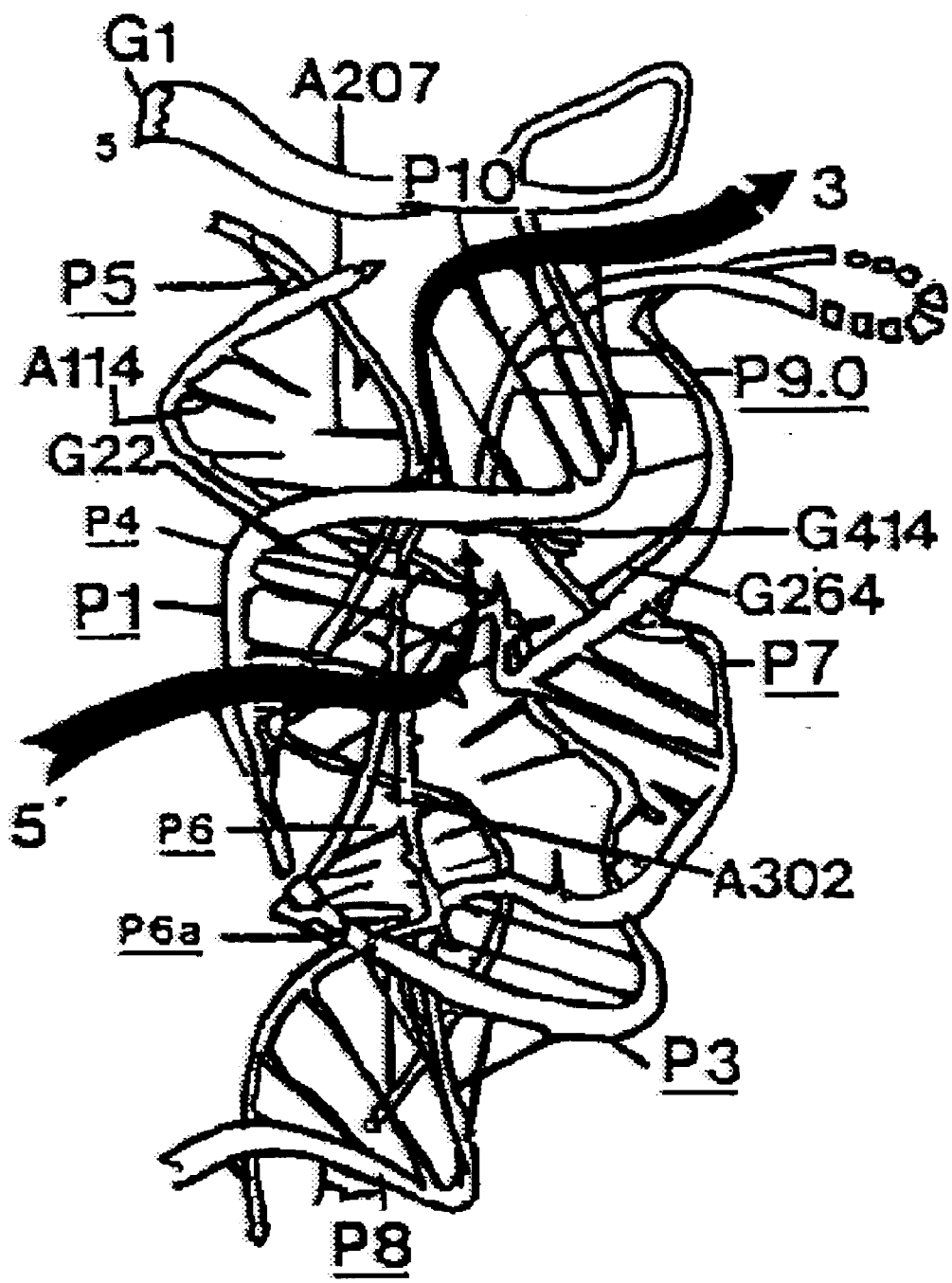
FIGS. 4A shows three dimensional structure of Group I intron ribozyme.
Figure 4B:
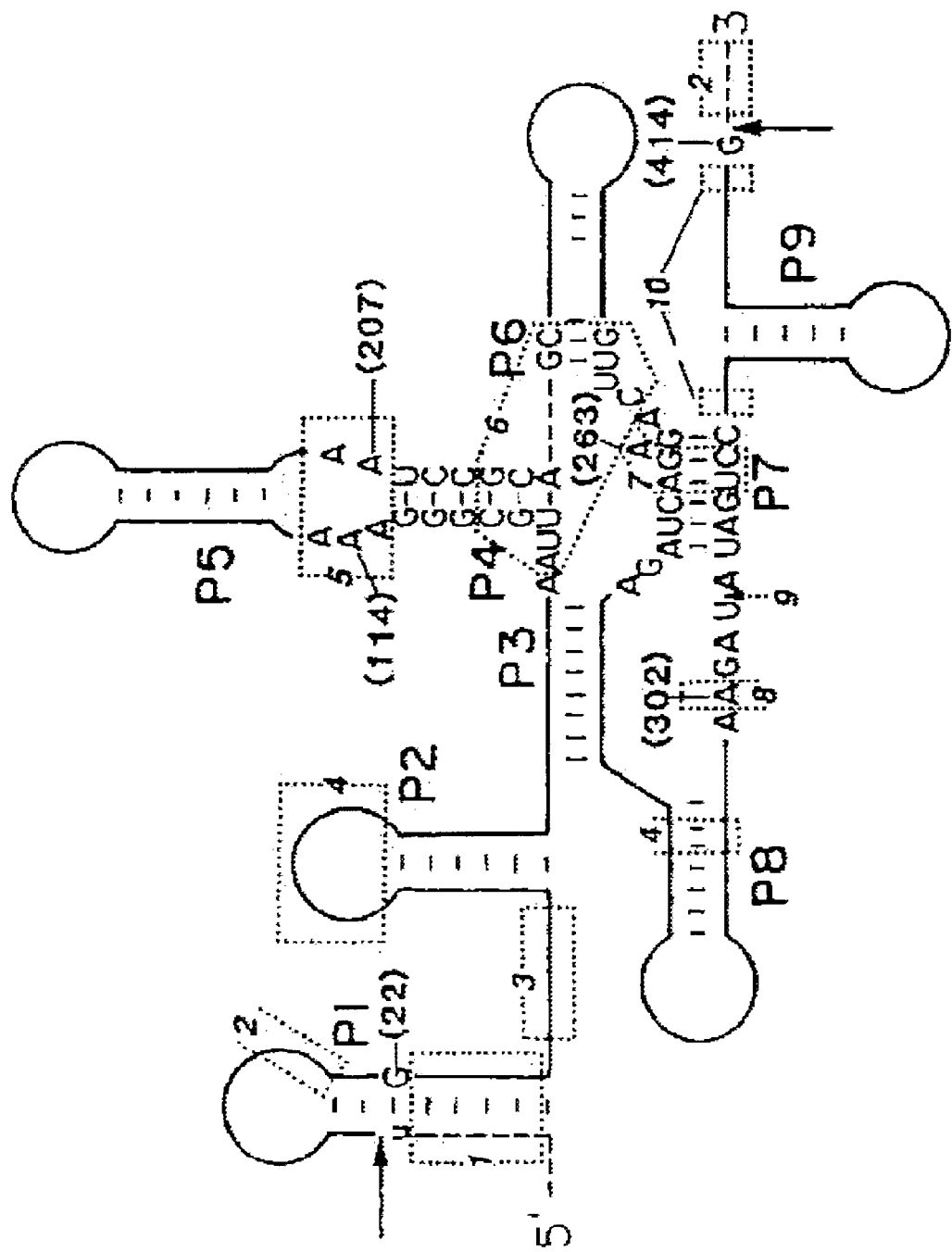
FIG. 4B shows the conserved nucleotide structure and secondary structure of Group I intron ribozyme.
Figure 4E:
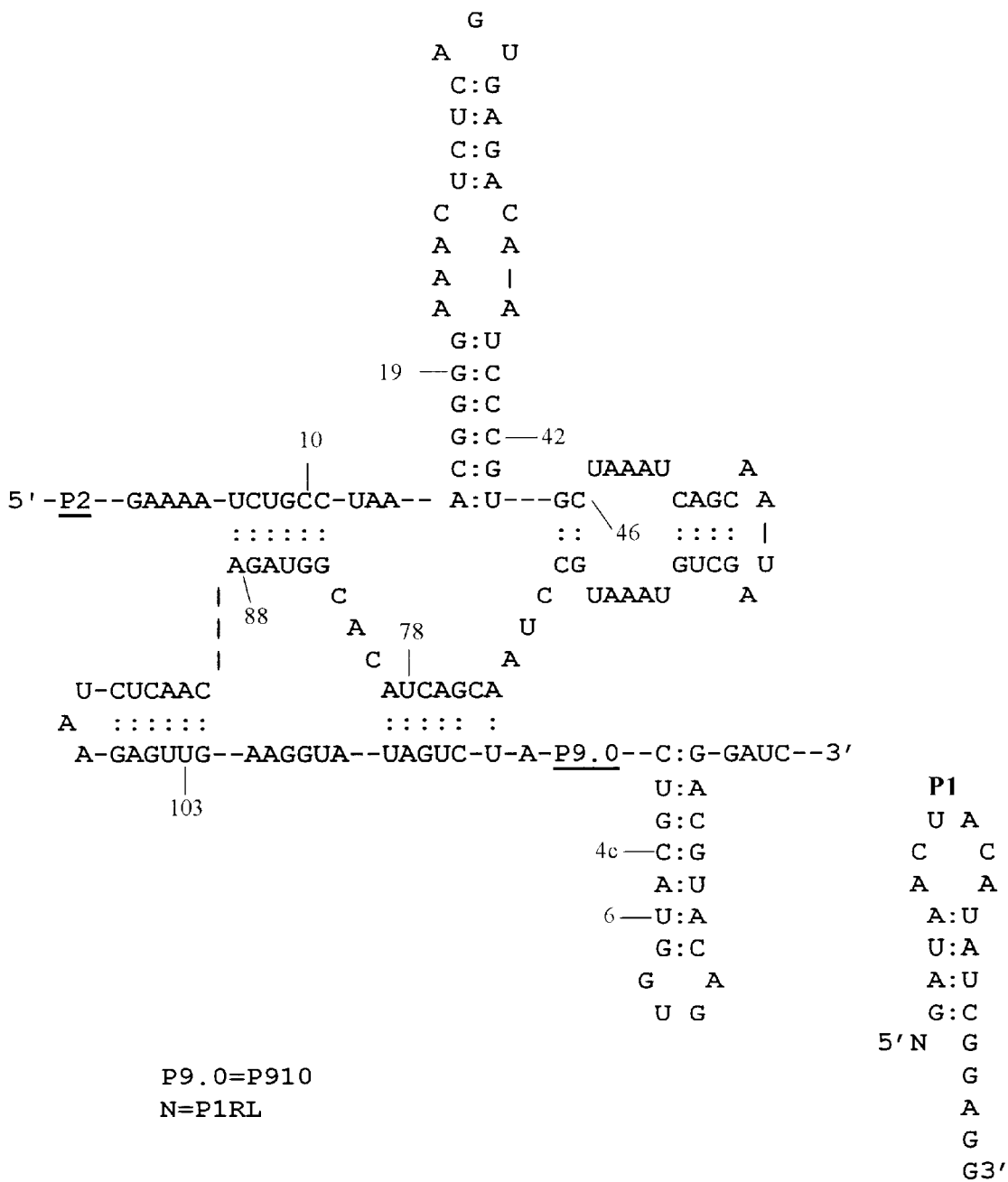
FIG. 4E shows various regions of SunY ribozyme P2 (SEQ ID No:28) and P1 (SEQ ID NO:29).

P1-shown in the right hand side of FIG. 4E
    P1=when N is G
    P1RL=P1 as in FIG. 4E when N=5' GGAGAAU 3'

P2-shown in the ribozyme of FIG. 4E
    P2A=A modification of P2 wherein the sequence 5' GGC UUA GAG AAG AAA UUC UUU AA 3' (SEQ ID NO:1) was inserted between #(−23) and 0
    P2H=A modification of P2 wherein the sequence 5' GGU AA 3' was inserted between #(×5) and 0

P5-shown in the ribozyme of FIG. 4E
    P5SA=A modification of P5 wherein the sequence 5' AGC UAU A 3' was inserted between bases #28 and #32
    P5LA=A modification of P5 wherein the sequence 5' AGC UAU AGA CAA GGC AAU CC 3' (SEQ ID NO:2) was inserted between bases #28 and #32

P9.0-shown in the ribozyme of FIG. 4E
    P9L=A modification of P9.0 with the sequence 5' AUU CUC 3'
    P910=A modification of P9.0 with the sequence 5' AUU CUC CAC C 3' (SEQ ID NO:3)
    P9A=A modification of P9 with the sequence 5' AAA GCC AAU AGG CAG UAG CGA AAG CUG CGG 3' (SEQ ID NO:4)
    [substitution of P9 after the P9.0]
    P9JD=A modification of P9 with the sequence 5' GGG GUG ACC CGA UC 3' (SEQ ID NO:5)
    [substitution of P9 after the P9.0]

F910-a 10 base pair sequence derived from F9 having a sequence: 5' AUU CUC CAC C 3' (SEQ ID NO:6).

The following are a list of chimeras of various SunY constructs used herein:

TABLE 1

| | Sun Y chimera name | Regions of Sun Y which were modified | | | |
|---|---|---|---|---|---|
| | | P2 | P5 | P9.0 | P9 |
| | | The modifying sequences | | | |
| 1 | Sun Y P9L | — | — | P9L | — |
| 2 | Sun Y P2P9L | P2A | — | P9L | — |
| 3 | Sun Y P910 | — | — | P910 | — |
| 4 | Sun Y P2P910 | P2A | — | P910 | — |
| 5 | Sun Y P2HP9L | P2H | — | P9L | — |
| 6 | Sun Y P9A | — | — | P9L | P9A |
| 7 | Sun Y P9JD | — | — | P9L | P9JD |
| 8 | Sun Y P3P9JD | P2A | — | P9L | P9JD |
| 9 | Sun Y P5SAP9L | — | P5SA | P9L | — |
| 10 | Sun Y P2P5SAP9L | P2A | P5SA | P9L | — |
| 11 | Sun Y P2HP5SAP9L | P2H | P5SA | P9L | — |
| 12 | Sun Y P5LAP9L | — | P5LA | P9L | — |
| 13 | Sun Y P2P5LAP9L | P2A | P5LA | P9L | — |
| 14 | Sun Y P2HP5LAP9L | P2H | P5LA | P9L | — |

EXAMPLES

In the following Examples, the numbers in brackets indicate the number of the relevant step in the respective figure.

Example 1

In Vitro Evolution Where the Co-factor is a Protein i. Preparing Random Panel of Nucleic Acid Sequences (1)

A random panel of DNA sequences is prepared on a standard nucleic acid synthesizer using a program for generating random sequences.

Figure 1:
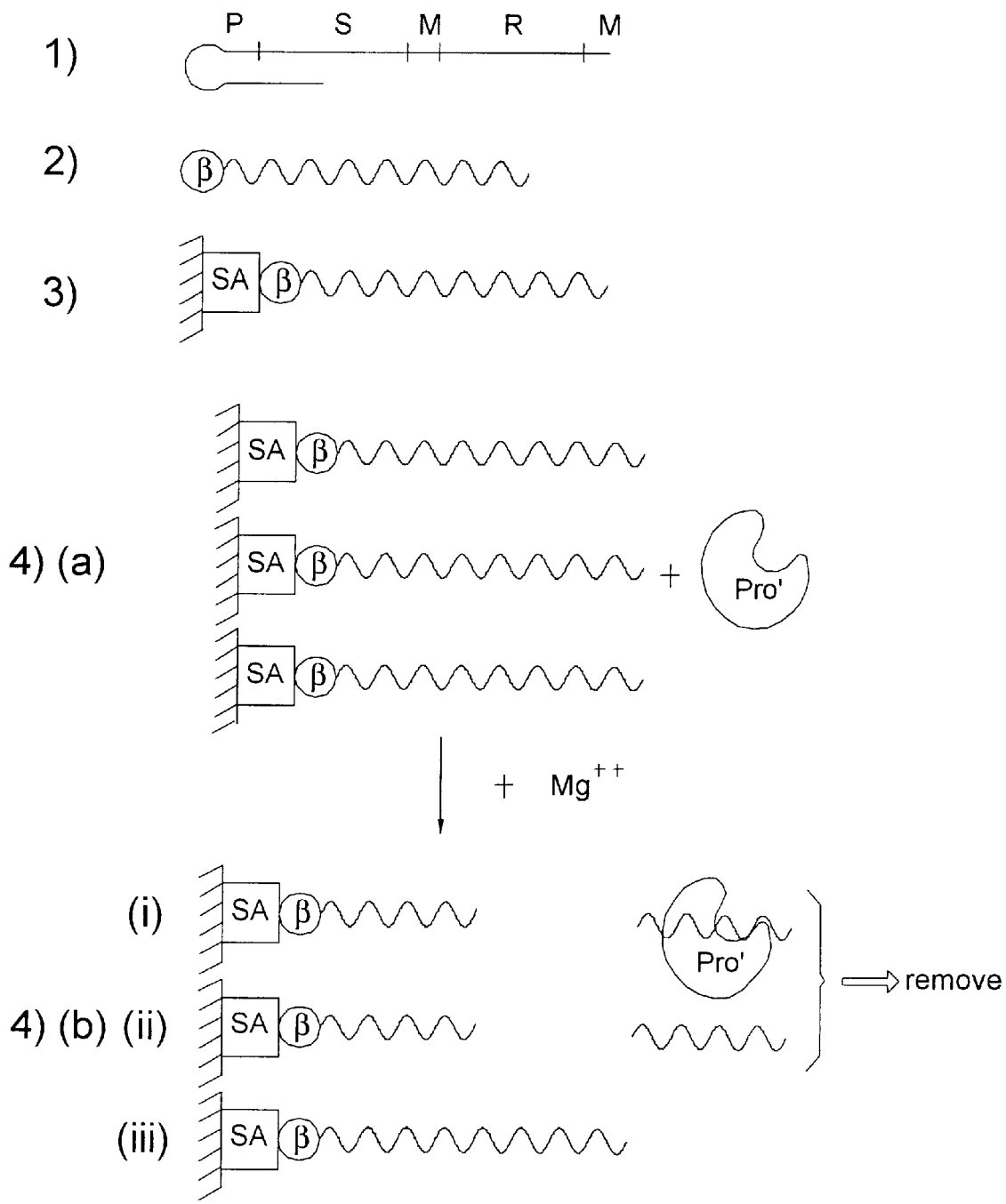
FIG. 1 shows a schematic representation of a method of preparing a proto-nucleozyme of the invention, where the specific co-factor is a protein.

A typical sequence is shown in FIG. 1 step (1) and comprises a promoter (P) of about 20 b.p., a sequence which is cleavable in cis by a catalytically active ribozyme termed in the figure "substrate" (S) of about 10 b.p. (both these sequences are constant and not random), a random generated sequence (R) of 50–8000 b.p. averaging at 100, and two sequences, one upstream of the random sequence and one downstream thereof, which serve as primer for PCR (M).

ii. Preparation of immobilized nucleic acid sequences (2 and 3)

The DNA sequences of i. above, are transcribed, using a primer with biotin (B) at the 5' end (FIG. 1, step 2). The biotin, is then allowed to react with avidin which is present on a solid support, such as Stepravidin beads (SA), so that each molecule of the random array becomes immobilized onto a solid support (FIG. 1, step 3).

iii. Negative Selection Step (4 and 5)

A reaction mixture is added to the nucleic acid sequences prepared above which lacks the assayed co-factor protein but contains magnesium ions which are necessary for ribozyme catalytic activity. Alternatively, it is possible to add a reaction mixture which contains another protein (Pro') which is different than the intended specific co-factor (FIG. 1, step 4a). Molecules which may be required for a catalytic activity such as $Mg^{++}$ or GTP are then added to the reaction medium (FIG. 1, step 4b). Those nucleic acid sequences which are either spontaneously cleaved (step 4b(ii)) or possess a normal cleavage activity of ribozymes with the non-assayed co-factor (Pro') (step 4b(i)) are released to the medium and are removed. After this negative selection only nucleic acid sequences which do not show any activity are maintained (step 4b(iii)). Thus the subsequent reaction mixture contains only these sequences (obtained in step 4b(iii)).

iv. Positive Selection Step (5)

The specific co-factor is protein (Pro) is then added to the reaction mixture (FIG. 1, step 5a).

Magnesium is then added to the reaction mixture in order to allow for the catalytic cis cleavage activity of the random nucleic acid sequences (FIG. 1, step 5b).

The nucleic acid sequences in the medium may be divided into three groups, as shown in step 5b:

Group i. proto-nucleozymes of the invention which are activated only upon formation of a catalytic complex with the specific co-factor protein;

Group ii. nucleic acid sequences, which complex with the protein co-factor, but do not feature any catalytic activity;

Group iii. (comprising the majority of the nucleic acid sequences) nucleic acid sequences which did not complex with the protein co-factor.

The last step of the positive selection comprises removal of those nucleic acid sequences which were freed from the immobilized beads (Group i.).

v. Amplification of Separated Sequence (6)

Sequences selected in iv. above are amplified. The amplified products are transcribed, bound to biotin and attached to a solid support as specified in (ii) above.

Steps (2)–(6) are then repeated for about 10–100 cycles, whereby the reaction mixture is gradually enriched with the proto-nucleozymes having the novel activity of the invention, i.e. that they are catalytically active only in the presence of the specific co-factor protein. It should be noted that the positive selection step may precede the negative section step.

Example 2

Preparing Co-factor Binding Haptens

As a preliminary step before constructing the DNA sequence of step 1 (in FIG. 1), it is possible to find first short sequences (haptens) which are capable of binding the desired co-factor (protein).

The procedure for the preparation of such haptens is as follows:

1. Short random sequences (about 80 base pairs) are prepared, and allowed to react with the protein co-factor.

2. Those sequences which bind the protein co-factor are identified for example, by the use of antibodies against the protein, by absorption of a protein to a membrane capable of absorbing proteins, etc. and are separated from the other sequences which did not bind to the protein.

3. Sequences which were obtained in step 2 are amplified.

4. Steps 2 and 3 above are repeated for 10–30 cycles so that the reaction mixture is enriched with haptens capable of binding the specific protein co-factor.

These short haptens then serve as part of the random sequence (R) shown in step 1 of FIG. 1.

Example 3

Preparation of a Semi-random Nucleic Acid Sequences

Sometimes, for in vitro evolution purposes, it is desired that the newly prepared panel of sequences resemble to some degree a known sequence, for example that of a ribozyme. If for example, it is desired that the semi-random sequence has a 70% average similarly to a specific nucleic acid sequence, it is possible to provide the nucleic acid synthesizer instead of four pure solutions containing each of the nucleotides (A, T, G and C), with four bottles each containing a solution composed of 70% one nucleotide (for example A), and 10% of each of the other three nucleotides (10% G, 10% T and 10% C). By instructing the synthesizer to construct a sequence utilizing these four mixtures, it is possible to obtain a sequence which has a 70% similarity to a known sequence. Other percentages of similarity may of course be used.

Example 4

In vitro Evolution Where the Co-factor is a Nucleic Acid Sequence

Figure 2A:
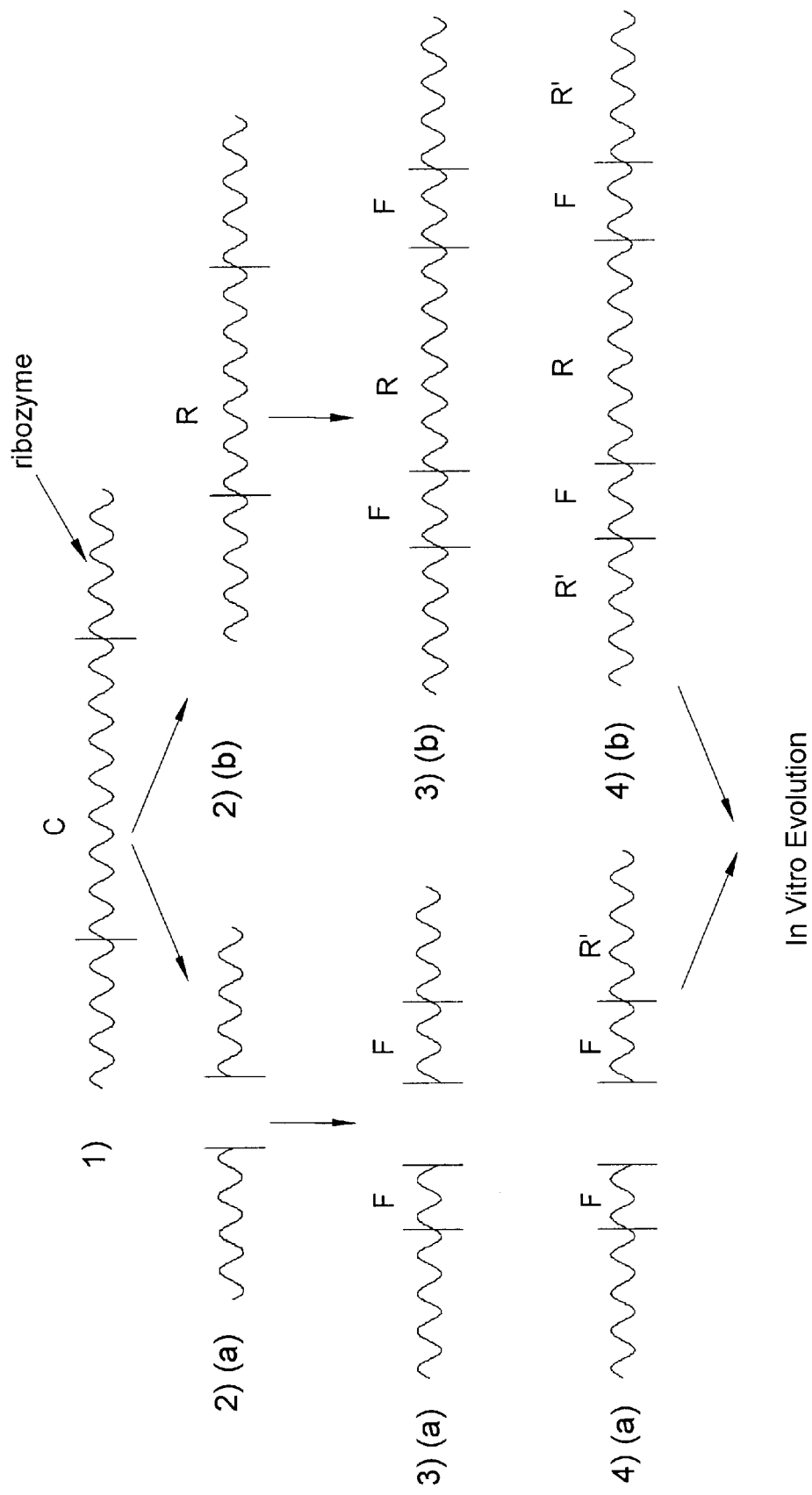
FIGS. 2A, 2B and 2C shows nucleic acid constructs which is a proto-nucleozyme where the co-factor is a nucleic acid sequence.

I. A Proto-nucleozyme for Use in the Detection of a Short Nucleic Acid Sequence Co-factor (FIG. 2A):

A known ribozyme sequence is chosen having a specific core region (C). The core region is screened for the sequences which most resemble the nucleic acid co-factor. The resembling sequences are removed altogether (FIG. 2, step 2a), or are replaced by a completely random sequence (R) (FIG. 2, step 2b).

The sequences upstream and downstream of the missing core region or the random region are fitted with two flanking sequences (F) which are complementary to the sequences which flank the intended co-factor (step 3(a) and (b)). The original ribozyme sequences of the ribozyme obtained by step 3(b) are then doped, i.e. to become semi-random (R') as explained in Example 3 (step 4(b)), for example by having a 70% similarity to the original ribozyme sequence.

As regards the two parts of the precursor obtained in step 3(a), only the original ribozyme sequence of one part is made to be semi-random (R') while the other part remains constant (step 4(a)).

The sequences obtained in 4(a) or 4(b) may then undergo the same steps of in vitro evolution of Example I (ii)–(v).

Figure 2B:
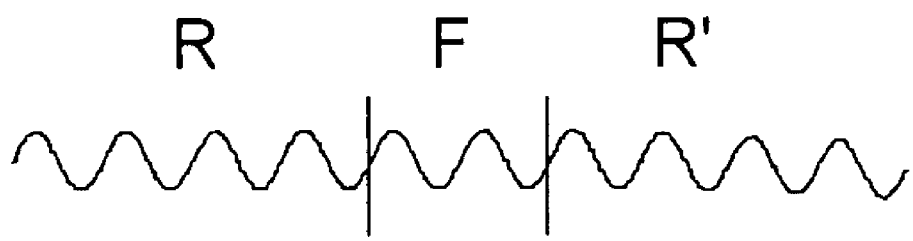
Figure 2C:
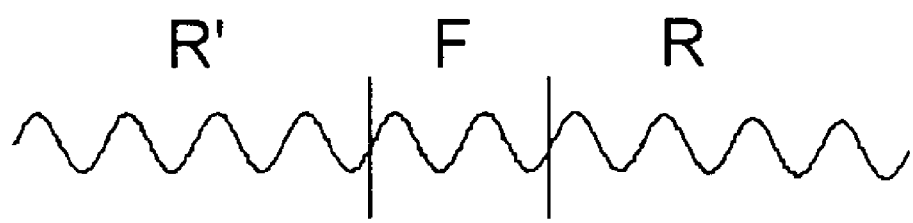

Alternatively, it is possible to construct a sequence comprising from 5'→3'; a completely random sequence (R), a flanking sequence (F) and a semi-random sequence (R') having a 70% similarity to a known ribozyme (FIG. 2B) or the same sequence in the 3'→5' orientation (FIG. 2).

II. A Proto-nucleozyme for Use With Detection of Long Nucleic Acid Sequence Co-factors The procedure of Example 4(I) above is essentially repeated, however, without inserting the flanking sequences (F) in the sequence. Since the co-factor to be detected is itself a very long nucleic acid sequence (for example ribosomal RNA), it is assumed that even without manipulation, some of the sequences of the long co-factor will be complementary (to some extent) to sequences of the core which have not been removed or replaced by random sequences.

III. A Proto-nucleozyme for Use in the Detection of a Nucleic Acid Sequence Co-factor Which is Unknown At times, it is not a priori known exactly what is the sequence of the target co-factor, for example, it may be one of many sequences of a virus or a bacteria the presence of which is to be detected. In such a case, it is best to randomly remove some sequences from the core of a ribozyme, and then render the remaining parts semi-random. It is desired that the removed sequences are completed by the sequences of the unknown bacteria.

When repeating steps (ii)–(v) of Example I with the construct prepared as above, it is necessary that in the negative selection, step (iii), the sequences of viruses or bacteria which are added to the reaction medium are similar to the one to be detected, in order to eliminate any nucleic acid sequences which are activated by other viruses or bacteria. In the repeating cycles, other types of viruses or bacteria may be added for the negative selection step.

Example 5

Improvement in Negative Selection Step Using a Tag Sequence i. Preparing Random Panel of Nucleic Acid Sequences (1)

A panel of DNA sequences is prepared on a standard nucleic acid synthesizer using a program for generating desired sequences.

A typical sequence is shown in FIG. 3 step (1) and comprises a promoter (P) of about 20 bases, a substrate S which can be cleaved in cis by a catalytically active oligonucleotide, a first primer for PCR amplification (PCR1), a first restriction site $C_1$ of about 4–8 bases, a random tag (TAG) sequence of about 15 bases, a second restriction site $C_2$ of about 4–8 bases (both these sequences are constant and not random), a variable sequence (V) of 50–8000 b.p. averaging at 100, said variable sequence being a candidate capable of evolving to a functional sequence. The variable sequence may be similar to variable sequences of other oligonucleotide species, for example since all sequences are doped, i.e. having a certain percent of nucleic acids identical with those of a known ribozyme and a certain percentage of randomness; and a second PCR primer sequence (PCR2). The variable sequence is a candidate for evolving to a sequence which after complexation with a specific co-factor, which completes a missing component becomes catalytically active.

ii. Preparation of Immobilized Nucleic Acid Sequences (2 and 3)

The DNA sequences of i. above, are transcribed, using a primer with biotin (B) at the 5' end (FIG. 3, step 2). The biotin, is then allowed to react with avidin which is present on a solid support, such as Streptavidin beads (SA), so that each oligonucleotide of the panel becomes immobilized onto a solid support (FIG. 3, step 3).

iii. Positive Selection Step (4)

The specific assayed agent which is a protein (serving as the selected set of conditions) (Pro) is then added to the reaction mixture (FIG. 3, step 4(a)).

Magnesium and/or other co-factors required for catalytic activity, are then added to the reaction mixture in order to allow for the catalytic cis cleavage activity of the variable sequences of the oligonucleotides on substrate sequence S (FIG. 3, step 4(a)).

The oligonucleotide sequences in the medium may be divided into three classes, as shown in step 4(b):

Class i. oligonucleotides activated only upon formation of a catalytic complex with the specific co-factor Pro and cleaved substrate S and are thus released to the medium;

Class ii. oligonucleotides, which feature catalytic activity even without a protein;

Class iii. (comprising the majority of the nucleic acid sequences) oligonucleotides which did not feature catalytic activity in the present co-factor.

The last step of the positive selection comprises collecting of those oligonucleotides which were freed from the immobilized beads (Class i. and Class ii.).

iv. Amplification of Separated Sequence (5)

If desired, protein attached to the oligonucleotides can be removed by denaturation through heating or by phenol-chloroform extraction.

Sequences collected in step 4 above are reversed transcribed and amplified by PCR. Since substrate sequence S was cleaved (step 4b) this sequence should be reconstructed by using, either for reverse transcription or for PCR proposes primers which contain the sequence of the cleaved substrate and tus the amplified and reconstructed product is again identical to 1. The amplified products are transcribed, bound to biotin and attached to a solid support as specified above (step 6).

v. Negative Selection Step (7)

The amplified and immobilized oligonucleotides of step 6 are subjected to a negative selection step. In this step the catalytic activity is determined either in the absence of any protein, or in the presence of non-co-factor agents, similar to the specific co-factor which is added to the reaction mixture, the agents being a protein similar to the specific co-factor (Pro') (step 7a); magnesium and/or other reagents required for catalytic activity are added (step 7b).

The oligonucleotides released to the medium by cleavage of the substrate sequence S belong to three classes:

Class i. in which the non-co-factor protein brought about cleavage of substrate sequence;

Class ii. which includes oligonucleotides cleaved with no need for any external co-factor whatsoever; and Class iii. which are not cleaved at all.

Both Classes i. and ii. are collected (step 7c) and the protein is removed (step 7d). The sequences are reversed transcribed and amplified by PCR in order to produce a double-stranded construct (step 8). Suitable restriction enzymes are added in order to cleave sequences $C_1$ and $C_2$, one cleavage site forming a blunt end and one a sticky end (step 9). The sticky end is completed with the aid of biotinated nucleotides and then the separated TAG sequence is immobilized on a solid support (avidin) and denaturated so that there remains a single-stranded denaturated immobilized tag sequence.

The immobilized tag sequences of step 10 are brought into contact with oligonucleotides collected of step 4(b) (Class i. and Class ii.) (step 11). Molecules of said group which hybridize with the immobilized TAG sequence are removed (step 12) so there remain only molecules which feature cleavage in the presence of the specific co-factor (Pro) and do not feature cleavage activity without any protein or in the presence of a non-co-factor agent (Pro').

The oligonucleotides obtained in step 11 are subjected again to all preceding steps for 2–1000 cycles, preferably 10–100 cycles, most preferably 20–30 cycles.

Example 6

Ligation of Substrates PIRL and 6.2: Comparison Between 15 Different SunY Ribozymes A comparison of the ability to ligate the substrates PIRL and 6.2 was carried out between the following 15 SunY-derived ribozymes:

| ■ SNYP9L; | ■ SNYP2AP9JD; |
|---|---|
| ■ SNYP2P9L; | □ SNYP5SAP9L; |
| □ SNYP910; | ■ SNYP2P5SAP9L; |
| □ SNYP2P910; | ■ SNYP2HP5SAP9L; |
| ■ SNYP2HP9L; | ■ SNYP5LAP9L; |
| ■ SNYP2AP9A (up); | ■ SNYP2P5LAP9L; |
| □ SNYP2AP9A (down); | ■ SNYP2HP5LAP9L; |
| ■ SNYP9JD; | ■ SNYP9L |

The Reaction Conditions were as follows:

Molar Ratio Ribozyme: PIRL:6.2=1:5:5

Final Ribozyme Concentration: 0.5 µM.

The reaction mixture containing the ribozyme, PIRL, and the 6.2 substrate was preincubated at 58° C. for 2 minutes in a buffer containing 30 mM tris-HCl, pH 7.4 (at 25° C.)/10 mM $NH_4Cl$/0.4 M KCl/20% ethanol. The solution was cooled to 45° C. and the reaction started by the addition of 90 mM final $MgCl_2$ in a reaction volume of 5 µl. The reaction was stopped after 30 minutes by the addition of 10 µl 2×loading buffer containing 7 M urea. Samples were heated for 2–3 minutes at 80° C. and loaded onto a 20% PAA gel containing 7 M urea. The radioactive gels were analyzed with the aid of a Biorad Phosphoirnager System.

Figure 5:
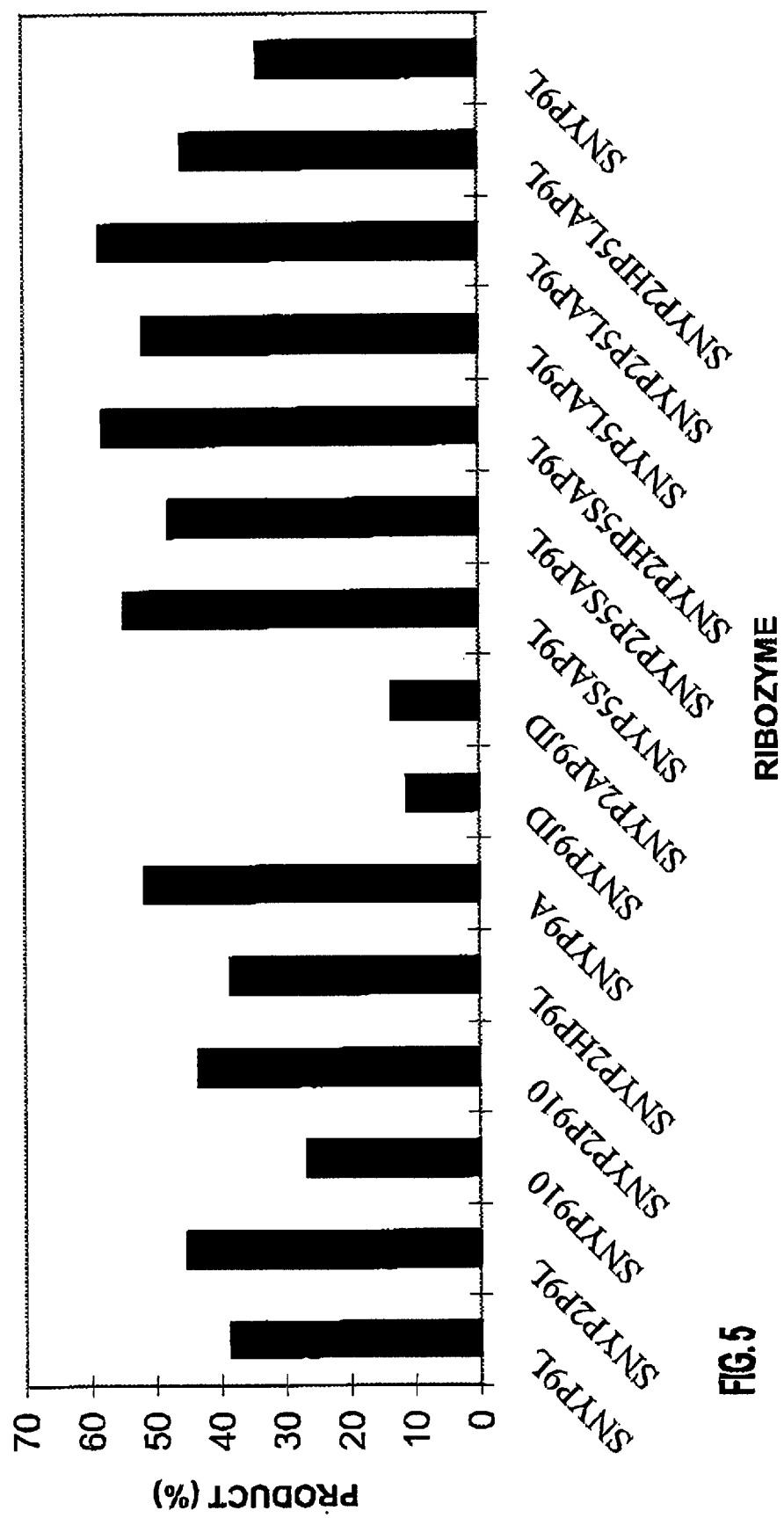
FIG. 5 shows a comparison in ligation product yield (%) between different SunY constructs.

The results are shown in FIG. 5. As can be seen, various ribozymes which were derived from the SunY ribozyme maintain the ability to ligate substrates.

Example 7

Kinetic Studies on Ribozymes SunY P910 Using the Substrates PIRL and 6.2

Ribozyme SunY P910 was used for ligation of the PIRL and 6.2 substrates.

The Reaction Conditions were as follows:

Molar Ratios between Ribozyme: PIRL:6.2=1:2.5:2.5 to 1:20:20

Final Ribozyme Concentration: 0.25 µM.

The reaction mixture containing the ribozyme and the substrates PIRL and the 6.2 was preincubated at 58° C. for 2 mins. in a buffer containing 30 mM tri-HCl pH 7.4 (at 25° C.)/10 mM $NH_4Cl$/0.4 M KCl/20% ethanol. The solution was cooled to 45° C. and the reaction started by the addition of 90 mM final $MgCl_2$ concentration in a final reaction volume of 5 µl.

At the designated times the reactions were stopped by the addition of 10 µl 2×loading buffer containing 7 M urea. Samples were heated for 2–3 minutes at 80° C. and loaded onto a 20% PAA gel containing 7 M urea.

Figure 6:
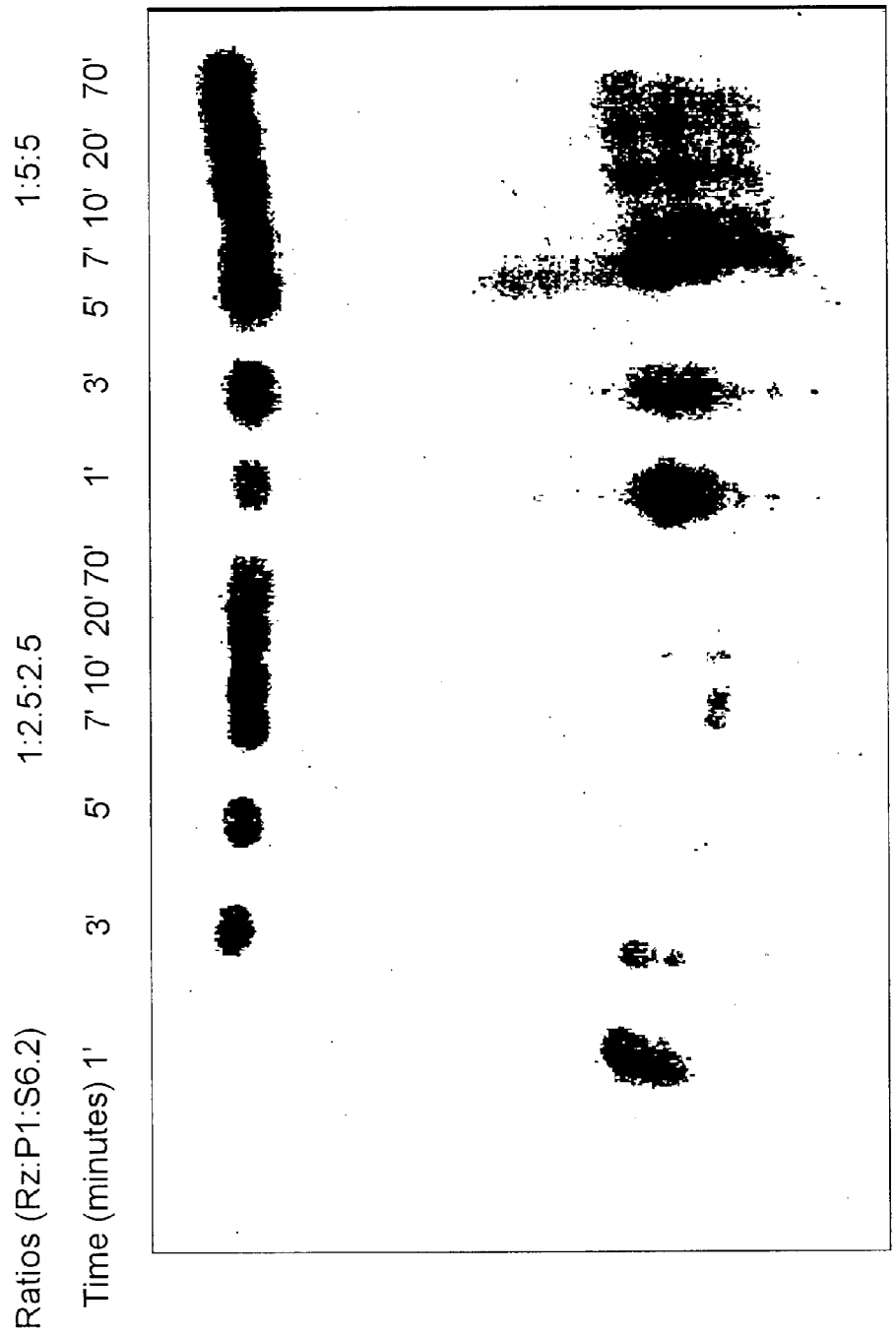
FIGS. 6 and 7 show electrophoresis gels of the ligation products of ribozymes in different experiments obtained by utilizing varying ratios of ribozymes to substrates taken at different times.
Figure 7:
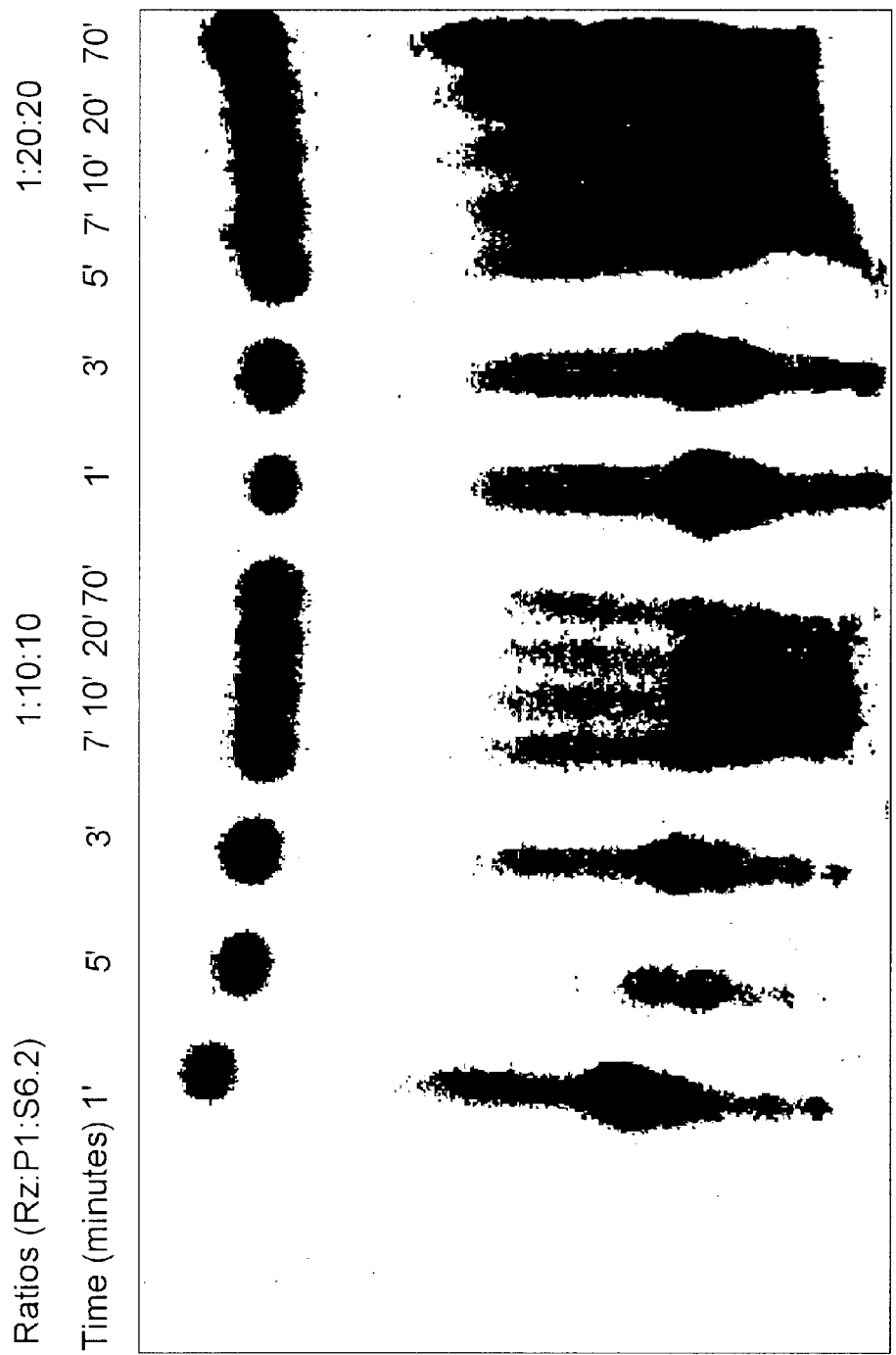

The radioactive gels were analyzed in a Biorad Phosphoimager system. The results are shown in FIGS. 6 and 7.

Figure 8:
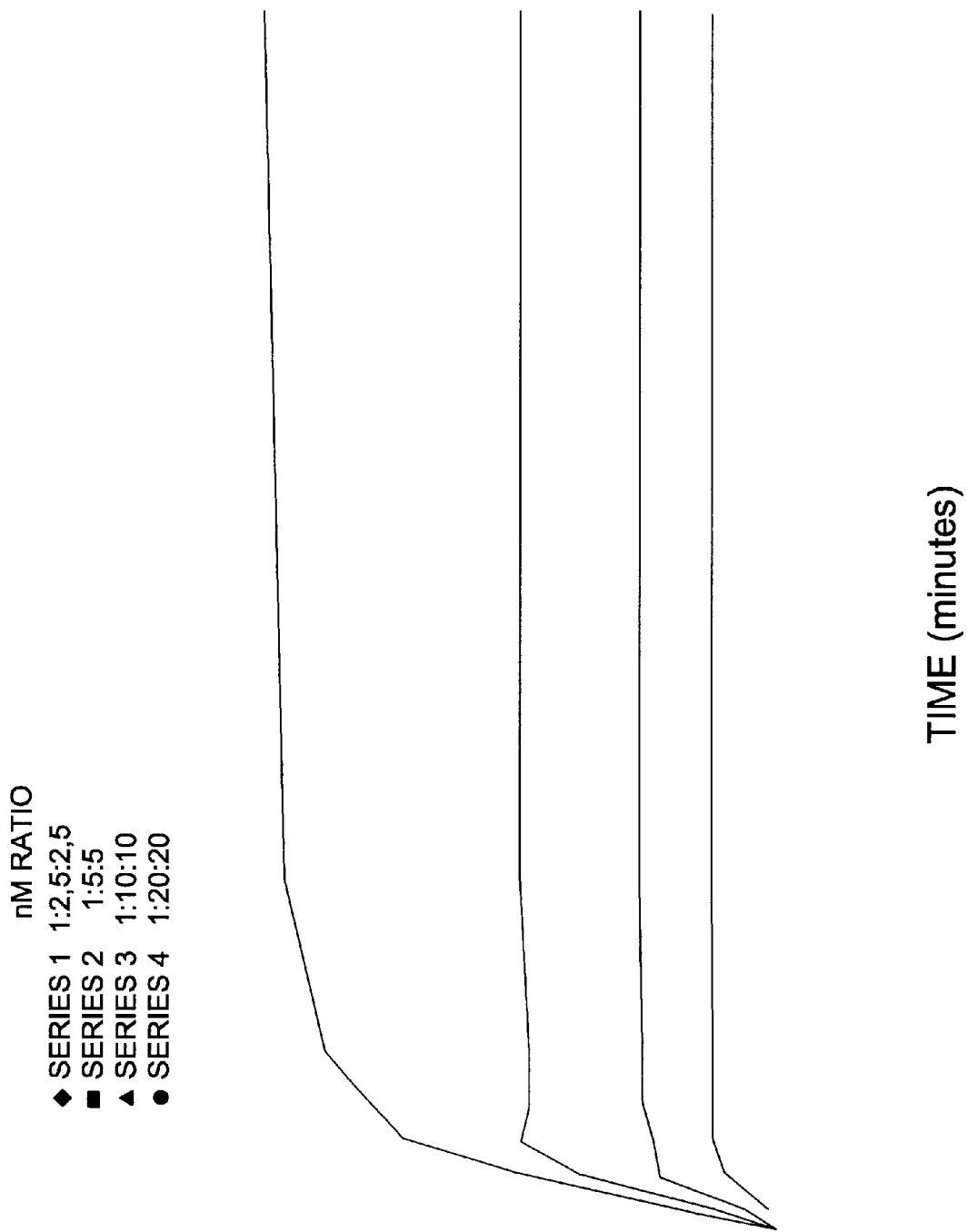
FIG. 8 shows a plot of the concentration ligation product (nM) created by a SunY P910 ribozyme at different ratios of ribozyme to the substrate as a function of time.
Figure 9:
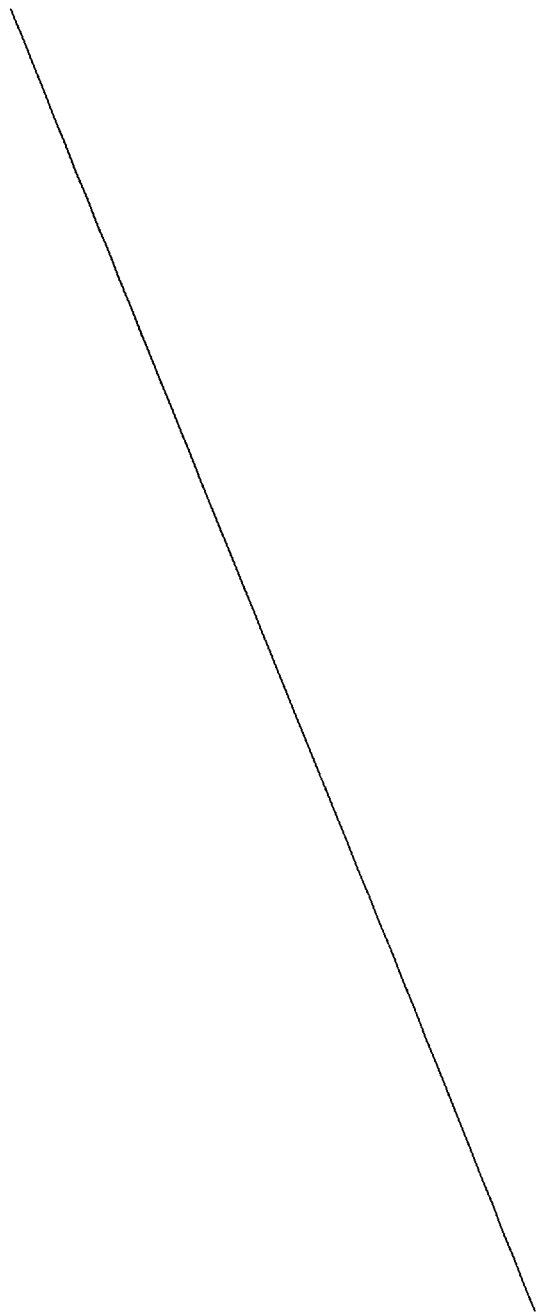
FIG. 9 shows double reciprocal (or Lineweaver Burt) plot based on the parameters of FIG. 8.

These results were used to plot kinetic graph depicted in FIG. 8, which was used to create Lineweaver-Burt Plot of FIG. 9. The calculated Km was 4.7 µm and the calculated $K_{cat}$ was 6 $min^{-1}$. These results indicate a vast improvement in Km and a 1800 improvement in $K_{cat}$ as compared to results obtained previously (data not shown) with the native SunY ribozyme.

Example 8

Effect of lysis Conditions on Ribozyme Kinetics

Conventional amplification systems are based on protein enzymes. Therefore, either tedious purification steps are necessary or very special and mild lysis conditions have to be worked out. In contract, ribozyme reactions are very robust and insensitive to harsh conditions, like:

high concentrations of the strong, ionic detergent SDA (up to the limit of solubility: 5% at 45° C. in the presence of 400 mM KCl)

high concentrations of the nonionic detergent Triton X-100 (10% at 45° C. are even stimulatory)

denaturing agents like urea (100 mM has no effect)

the nuclease inhibitor EDTA the ribonuclease inhibitor ATA organic solvents like isopropanol, ethanol.

The Effects of all additives on ribozyme reactions were analyzed by polyacrylamide gel electrophoresis and are shown hereinbelow. in which Fragment A is SEQ ID NO:33, Fragment B is SEQ ID NO:34, a and Fragment C is SEQ ID NO:35

I. Effect of Denaturating Agents (SDA, GITC, Urea and Phenol) on Ribozyme Reaction Rate Reaction conditions:

0.5 $\mu$M and 5 $\mu$M P1 BS and 5 PM $^{32}$P-labeled 6.2 substrate were incubated at 58° C. in reaction buffer containing SDS, GITC, urea or chloroform in concentrations indicated in FIG. 9 or 25% (v/v) of the aqueous supernatant above the phenol or phenol/chloroform phase. The arrow at the top of the figure indicates a re-extraction of the aqueous phase with chloroform; again 25% of the aqueous supernatant was added to the ribozyme reaction. After slow cooling down to 45° C. the reaction was started by the addition of MgCl$_2$ to a final concentration of 150 mM. After 60 mins. the reaction was stopped by quenching with 8 M urea.

Figure 10:
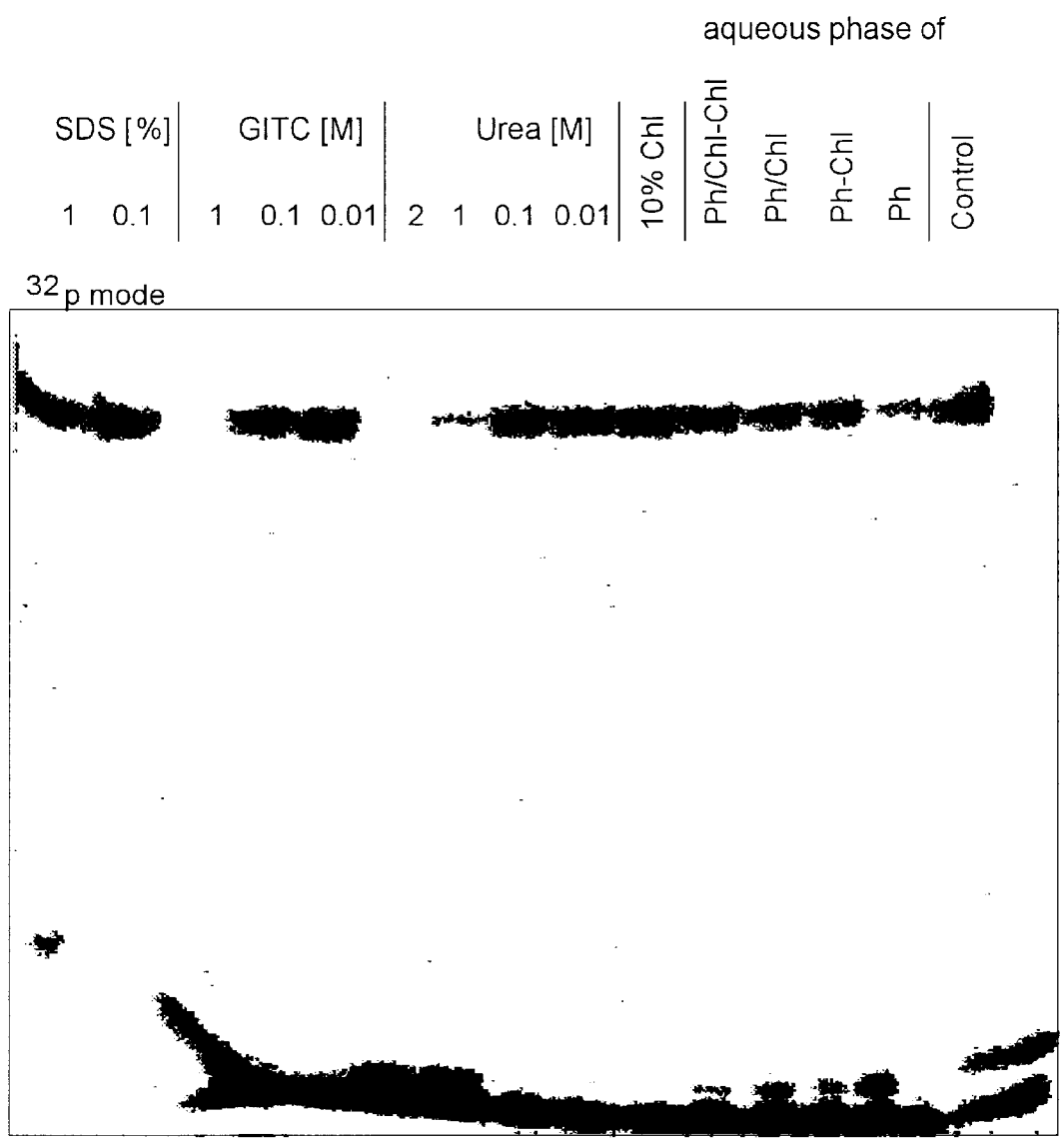
FIG. 10 shows the effects of various concentrations of SDS, GITC, urea and phenol (re-extracted with chloroform) or ribozyme reaction.

The results are shown in FIG. 10. As can be seen, addition of denaturing agents or phenol after re-extraction with chloroform did not significantly change the ribozyme as compared to control.

Figure 11:
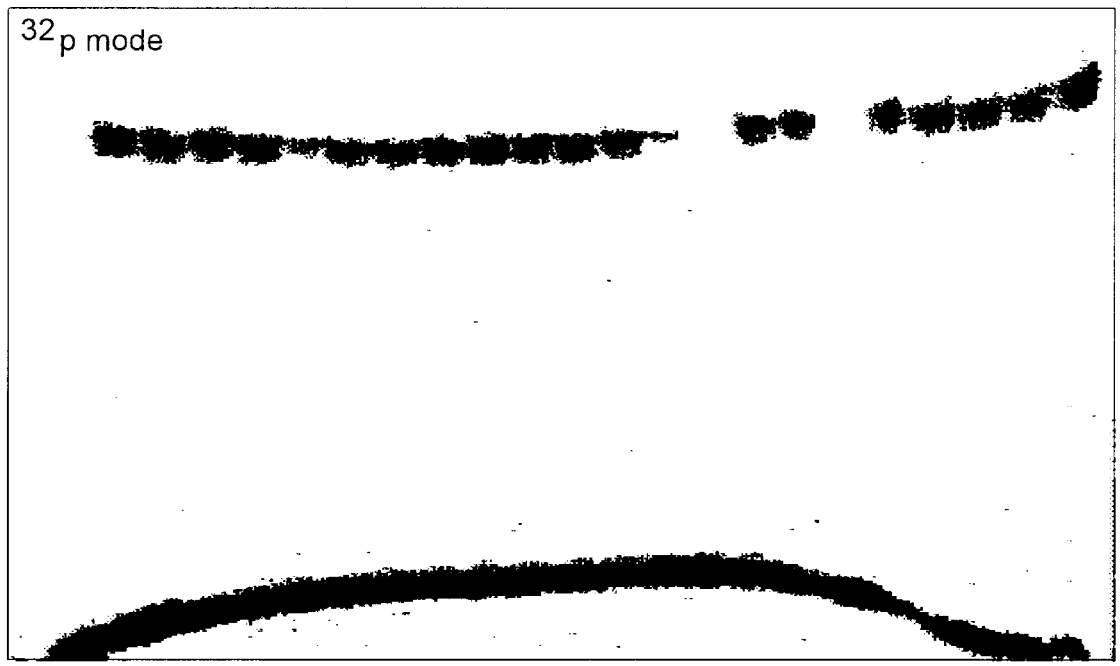
FIG. 11 shows the effect of varying concentrations of the PCR inhibitors isopropanol, EtOH, urea, GITC and SDS on ribozyme reaction.

II. Effect of PCR Inhibitors (isopropanol, EtOH, Urea, GITC and SDS) on Ribozyme Reaction Rate 0.5 $\mu$M SunY and 5 $\mu$M $^{32}$P-labeled 6.2 substrate and 5 $\mu$M PI BS were preincubated at 58° C. in reaction buffer containing the indicated concentrations of various PCR inhibitors (EtOH as indicated, all others contain 10% EtOH) and slowly cooled down. After the reaction reached 45° C., the reaction was started by addition of MgCl$_2$ to a final concentration of 150 mM. After 60 mins. the reaction was stopped by quenching with 8 M urea. The results are shown in FIG. 11.

As can be seen, various agents which inhibit PCR reactors do not significantly effect ribozyme-based reactions, thus making ribozyme-based reaction agents more attractive for detection purposes.

III. Effect of Phenol and Commercial Specimen Preparation Kit on Ribozyme Reaction Rate 0.5 $\mu$M SunY and 5 $\mu$M PI BS and 5 $\mu$M $^{32}$P-PIP were preincubated at 58° C. in reaction buffer containing the following additives: 25% (v/v) of the aqueous layer above phenol or phenol/chloroform. The arrow indicates a re-extraction with chloroform; again 25% of the aqueous layer was added. The following solutions were added from the commerical Amplicor CT/NG kit (Chlamydia trachomatia/Nelsseria gonorrhoeae) Specimen Prep Kit (Roche): 25% or 10% (v/v) of Urine Wash Buffer; 25% or 10% of CT/NG Specimen Diluent; 25%, 10% or 8.3% of CT/NG Lysis Buffer which contains an unspecified, non-ionic detergent.

Figure 12:
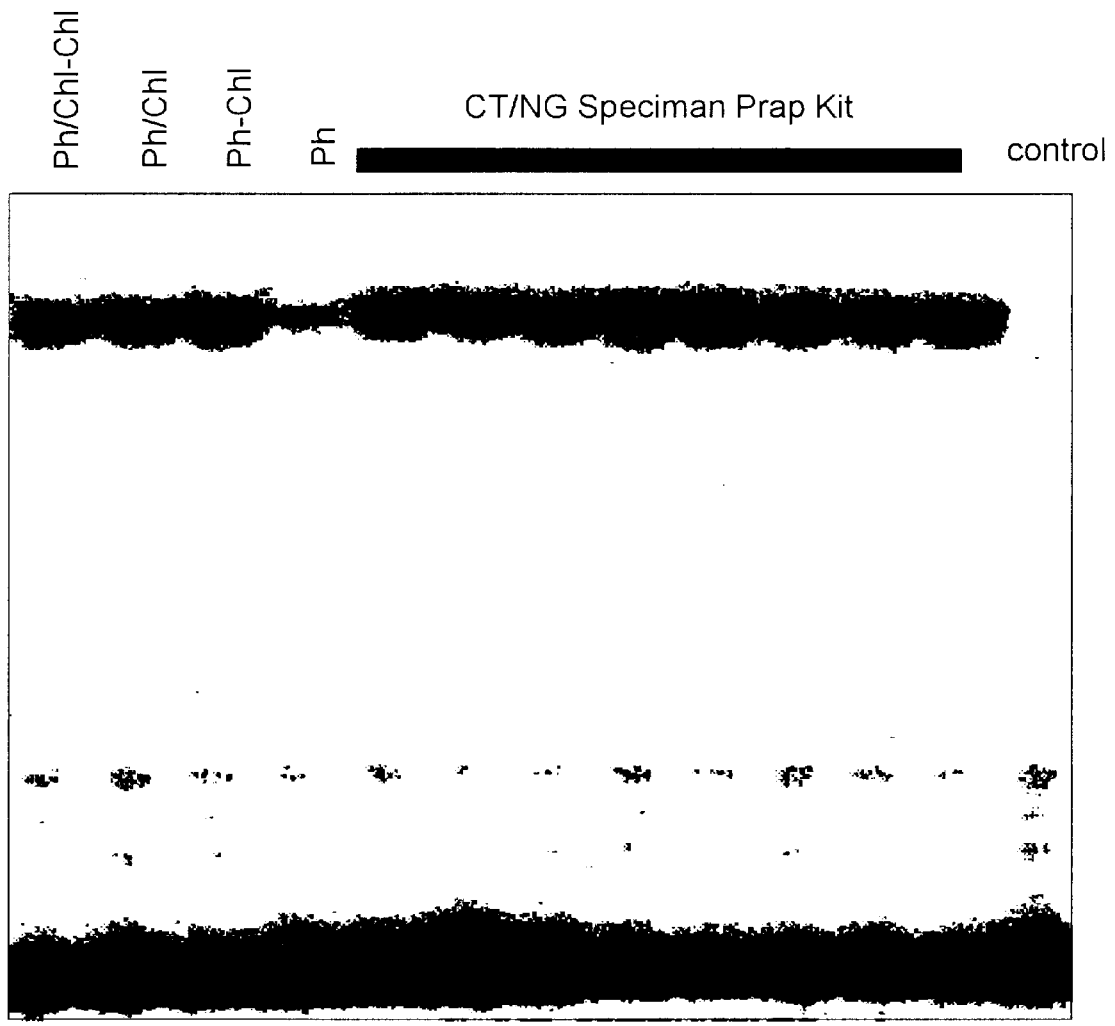
FIG. 12 shows the effect of phenol (either not extracted or re-extracted with chloroform) and a commercial specimen preparation kit, on ribozyme reaction.

After the temperature reached 45° C., the reaction was started by the addition of MgCl$_2$ to a final concentration of 150 mM. The reaction was stopped after 60 mins. by quenching with 8 M urea. The results are shown in FIG. 12.

As can be seen, both phenol, which is used heavily in various laboratories for specimen preparation, (after re-extracted by chloroform) and a commercially available specimen preparation kit did not effect the ribozyme reaction. Laboratory procedure carried out in the presence of phenol should include a re-extraction step by chloroform before submitting the specimen to ribozyme reaction.

IV. Effect of Varying Concentrations of GITC on Ribozyme Reaction Rate 0.25 $\mu$M SunY and 5 $\mu$M $^{32}$P-labeled 6.2 substrates and 5 $\mu$M PI BS were preincubated at 58° C. in reaction buffer containing GITC in 100 mM incremental from 0 to 1 M and slowly cooled down. After the temperature reached 45° C., the reaction was started addition of MgCl$_2$ to a final concentration of 150 mM. After 30 mins. the reaction was stopped by quenching with 8 M urea.

Figure 13:
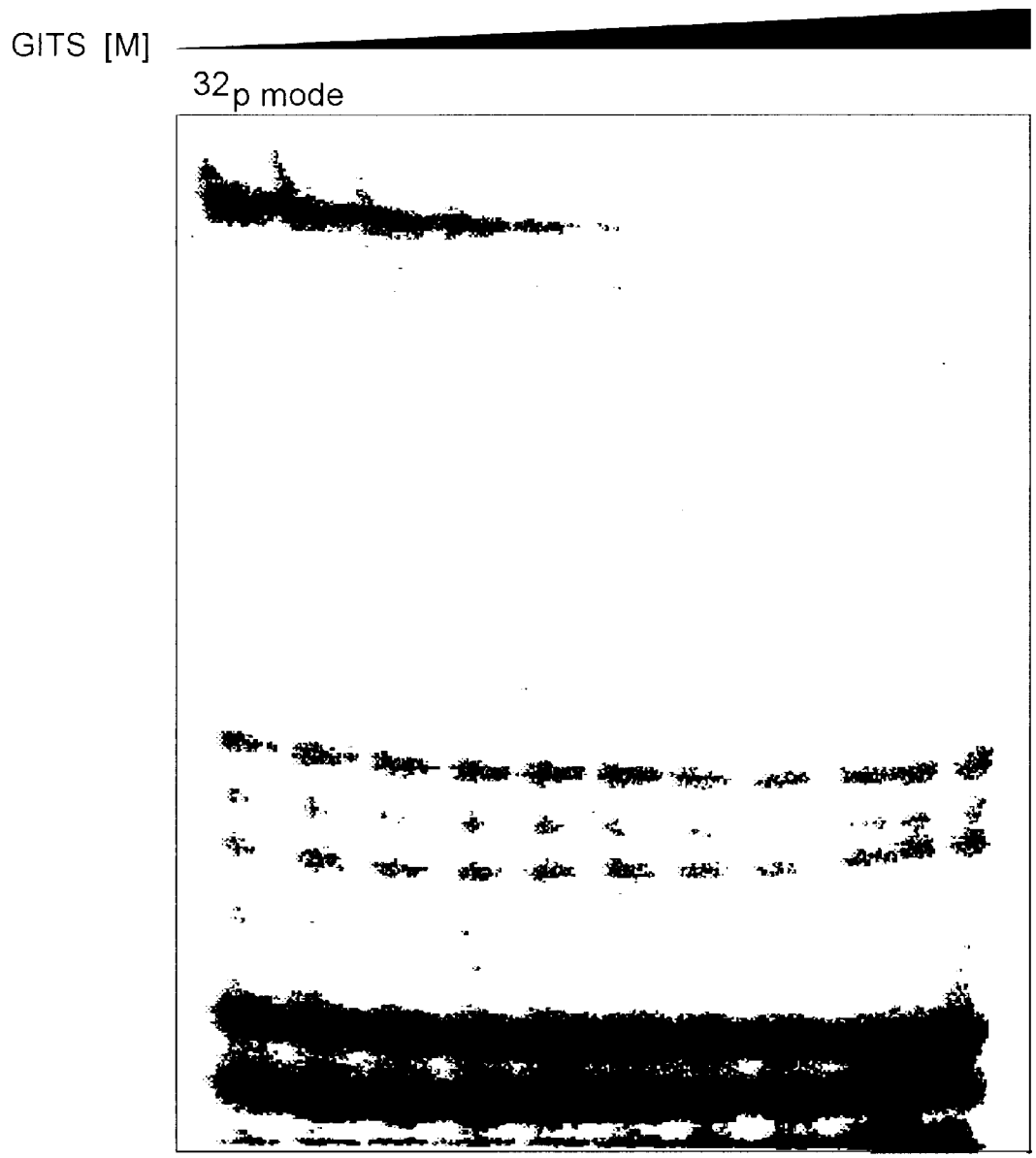
FIG. 13 shows the effect of varying concentrations of GITC on ribozyme reaction (expansion of FIG. 10)

The results are shown in FIG. 13. As can be seen up to 300 mM GITC did not effect the reaction rate.

V Effect of Various Additives (ATA, Spermidine, DMF, DMSO, Triton, Nonidet and Tween 40) on Ribozyme Reaction 0.5 $\mu$M SunY and 5 $\mu$M PI BS and 5 $\mu$M $^{32}$P-labeled 6.2 substrates were incubated at 58° C. in reaction buffer containing the indicated additives. After slow cooling to 45° C., the reaction was started by the addition of MgCl$_2$ to a final concentration of 150 mM. After 60 mins. the reaction was stopped by quenching with 8 M urea. Relative product yields are indicated: the value for the control without additive was set to 100. The significant stimulation with Triton X-100 is printed in bold.

Figure 14:
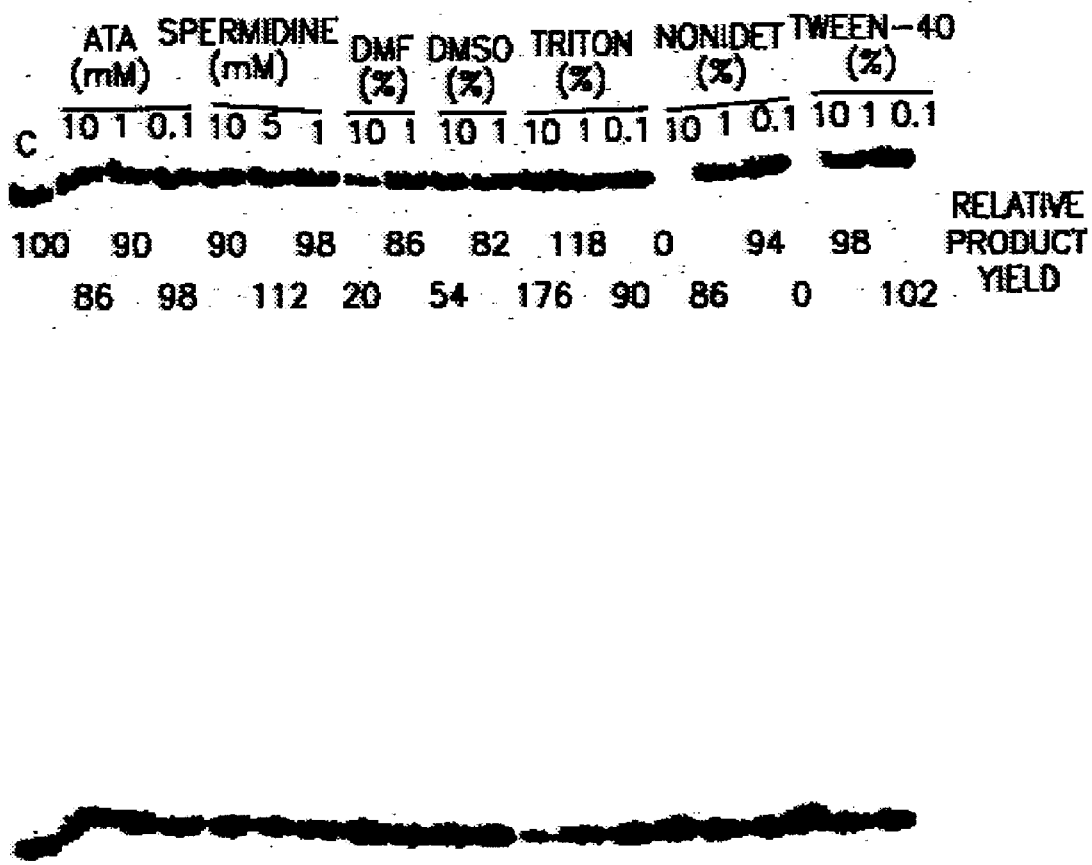
FIG. 14 shows the effect of varying concentrations of ATA, Spermidine, DMF, DMSO, Triton, Nonidet and Tween 40 on ribozyme reaction.

The results are shown in FIG. 14. As can be seen, most of the additives did not significantly reduce the ribozyme reaction while Triton X-100 increase ribozyme activity by 80%.

Figure 15:
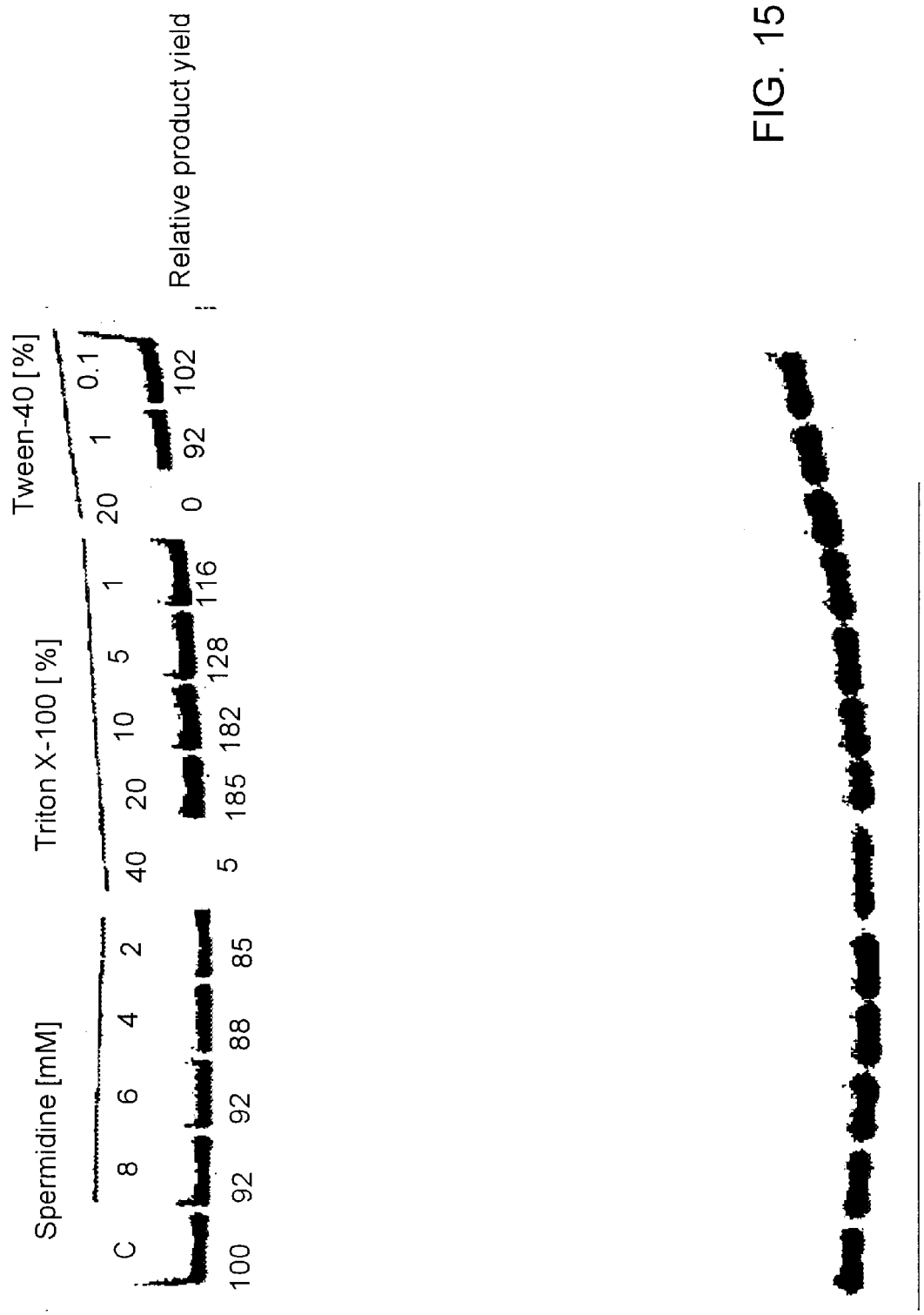
FIG. 15 shows the effect of varying concentrations of Spermidine, Triton X-100 and Tween 40 on ribozyme reaction (expansion of FIG. 14)
Figure 16:
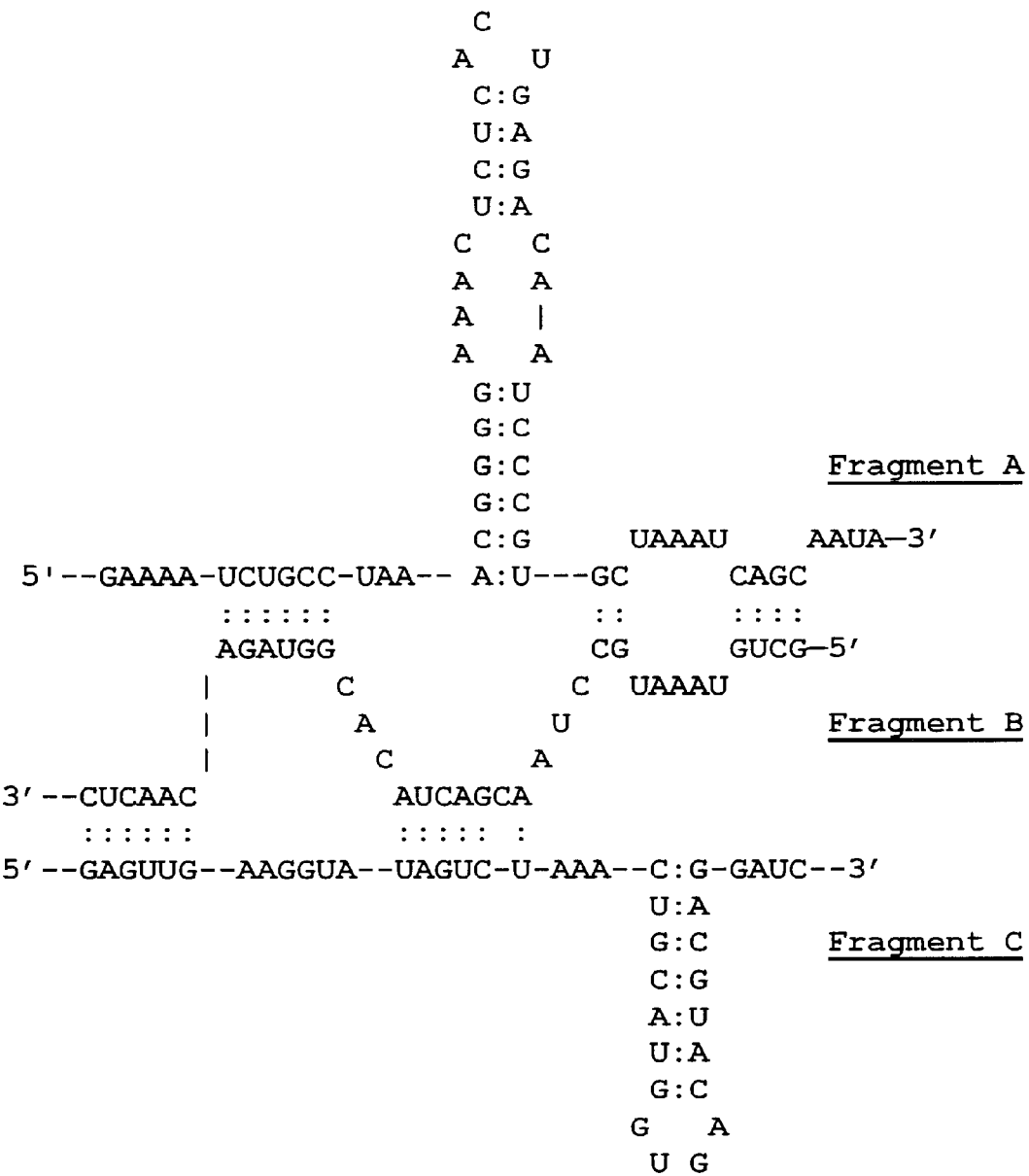
FIG. 16 shows the construct of the native SunY ribozyme in which Fragment A is SEQ ID NO:30, Fragment B is SEQ ID NO:31, and Fragment C is SEQ ID NO:32.
Figure 18:
FIG. 18 shows an electrophoresis gel indicating the ligation activity of various Group I intron chlamydia-based ribozymes.

VI. Effect of Additives (Spermidine, Triton X-100 and Tween 40) on Reaction Rates 0.5 $\mu$M SunY and 5 $\mu$M PI PS and 5 $\mu$ $^{32}$P-labeled 6.2 substrates were incubated at 58° C. in reaction buffer containing the additives indicated in FIG. 14. After slow cooling to 45° C., the reaction was started by the addition of MgCl$_2$ to a final concentration of 150 mM. After 60 mins. the reaction was stopped by quenching with 8 M urea. Relative product yields are indicated: the value for the control without additive was set to 100. The significant stimulation with Triton X-100 is printed in bold. The results are shown in FIG. 15.

As can be seen from the additives used, only Tween 40 at a concentration of 20% significantly inhibited the reaction. Triton X-100 at all concentrations tested was able to increase activity by 28% to 85%.

Example 9

Chalamydia-based Proto-nucleozymes (A) Part of the catalytic core of an evolved SunY ribozyme was substituted with 16s rRNA sequences from *Chlamydia trachomatis*. Corresponding changes were introduced in the ribozyme to accommodate the Chlamydia substitution. FIG. 16 shows the wild type ribozyme with the sequence to be substituted in bold print. 17 different ribozyme sequences were tested for splicing activity. FIG. 17 shows the actual sequence of the ribozyme (option 29) which is active when part of its core sequence was substituted by chlamydia sequences (the latter represented in bold).

The experiments were conducted as follows:

In FIG. 18, 2 $\mu$M of each of the 17 putative Chlamydia dependent ribozymes were reacted with 4 $\mu$M of substrate for 18 hours at 45° C. The wild type SunY ribozyme was used as positive control. Reactions were stopped with 5 mM EDTA and 3.5 M urea, final concentration, and then run on a 20% PAA-7M urea gel. The results are shown in FIG. 18.

These results show that a ribozyme (option 29) where part of its nucleotides were replaced by 16s rRNA sequences of *Chlamydia trachomatis* can be catalytically active. This ribozyme without the Chlamydia sequence can serve as a proto-nucleozyme of the invention and used in an assay to detect the presence of chlamydia, since the Chlamydia sequences (serving as co-factors) can complete its missing sequences and thus form a catalytically active nucleozyme.

(B) C223 Targezyme

A proto-nucleozyme termed hereinafter the "C223 targezyme" is a ribozyme based on the sunY group I intron ribozymes. It is composed of two fragments that anneal to form an active enzyme. This ribozyme consists of a C fragment sequence originated from the 16S rRNA of *Chlamydia trachomatis* (referred as the target) and of an AB fragment (referred as the targezyme). A schematic view of this proto-nucleozyme is shown in FIG. 24.

The C223 targezyme was tested for its specificity to the target sequence. 67 bases long sequences from various organisms shown in Table 2 below were incubated at 45° C. for 2 hours with the targezyme molecule. Final concentrations of the reaction components were 2 mM of C223 targezyme, 2 mM of target, 5 mM of substrates, 30 mM Tris pH-7.4, 10 mM $NH_4Cl$, 0.4 M KCl, 10% ethanol, 90 mM $MgCl_2$.

Results are depicted in Table 3.

TABLE 2

67 base long sequences from various organisms

| Organism | Sequence |
|---|---|
| *C. trachomatis:* | CTTTCGGTTAAGGGAGAGTCTATGTGATATCAGCT(SEQ ID NO:7) AGTTGGTGGGGTAAAGGCCTACCAAGGCTATG |
| *C. Psittaci:* | CTTTCGGTTGAGGAAGAGTTTATGCGATATCAGCT(SEQ ID NO:8) TGTTGGTGGGGTAAAAGCCCACCAAGGCGATG |
| *C. pneumoniae:* | CTTTCGGTTAAGGGAGAGTCTATGGGATATCAGC (SEQ ID NO:9) TTGTTGGTGGGGTAATGGCCTACCAAGGTTTTG |
| *N. gonorrhoeae:* | CTTGCGCTATCCGAGCGGCCGATATCTGATTAGCT(SEQ ID NO:10) GGTTGGCGGGGTAAAGGCCCACCAAGGCGACG |
| *E. coli:* | CTCTTGCCATCGGATGTGCCCAGATGGGATTAGCT(SEQ ID NO:11) AGTAGGTGGGGTAACGGCTCACCTAGGCGACG |

The marked bases represent differences from the *C. trachomatis* sequence.

TABLE 3

Relative activity of targezyme in the presence of specific sequences

| Organism | Relative Activity (%) |
|---|---|
| *Chlamydia trachomatis* | 100 |
| *Chlamydia pneumoniae* | 4 |
| *Chlamydia psittaci* | ND |
| *Azoarcus calcoaceticus* | ND |
| *Escherichia coli* | ND |
| *Neisseria gonorrhoeae* | ND |

As can be seen from the above table C223 targezyme was very specific to *Chlamydia trachomatis* showing virtually no activity in the presence of sequences obtained from other organisms.

Example 10

Detection of Ribozyme Ligation Reaction Utilizing Fluorescence Energy Transfer (FRET)

A convenient model for detecting ribozyme activity, which may be cleavage, splicing or ligation is to use a fluorescent dye such as fluorescein (F) and a quencher dye CY-5. When the two dyes are brought together (for example, due to ligation or splicing), the reporter dye (F) can absorb light, but fluorescence is quenched by FRET: the energy is transmitted to the quencher dye CY-5 which emits its distinctly different fluorescence light at 670 nm. As a consequence of the ligation or splicing reaction, the F-labeled nucleotide(s) is/are liberated. Now, the reporter dye can emit its own, characteristic fluorescence at 522 nm.

Two small RNAs which are well characterized substrates for ligation by Group I ribozymes, were chosen.

Each RNA is labeled with only one dye:

the large RNA carries the "reporter" dye fluorescein (F) at its 5'-end;

the small RNA carries the "quencher" dye CY-5 at its 5'-end.

Both RNAs associate under reaction conditions.

Figure 19:
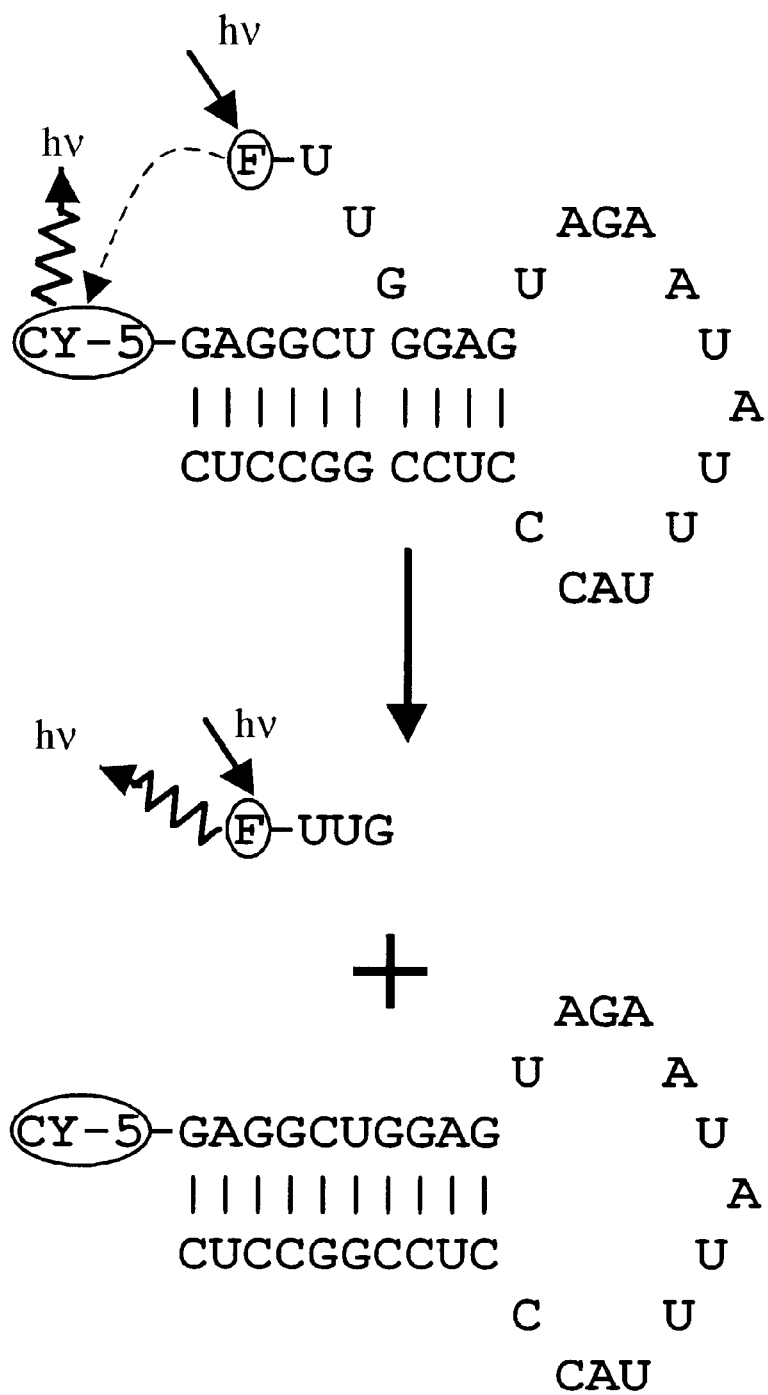
FIG. 19 shows fluorescent labeled RNA constructs used as ribozyme substrates (SEQ ID NO:36)

The ribozyme constructs are shown in FIG. 19.

Before the ribozyme reaction, both RNA substrates hybridize to form a nicked hairpin. Incoming light (hv; represented in the figure as a solid arrow) is absorbed by fluorescing (F) and transferred to CY-5 (dashed arrow) which subsequently emits its own characteristic fluorescence at 670 nM (hv; zigzag arrow).

After the reaction, the fluorescein-labeled trinucleotide (F-UGG) is liberated and the absorbed light is emitted directly from fluorescein with the characteristic wavelength of 522 nm.

Diagram 11: An Example of Real Time monitoring

FRET can be measured by calculating the ratio of the signal from the reporter dye F (at 522 nm) to an inert signal at 500 nm.

This ratio is plotted versus the time axis: After 5 minutes incubation intervals, fluorescence was measured for 30 seconds.

Figure 21:
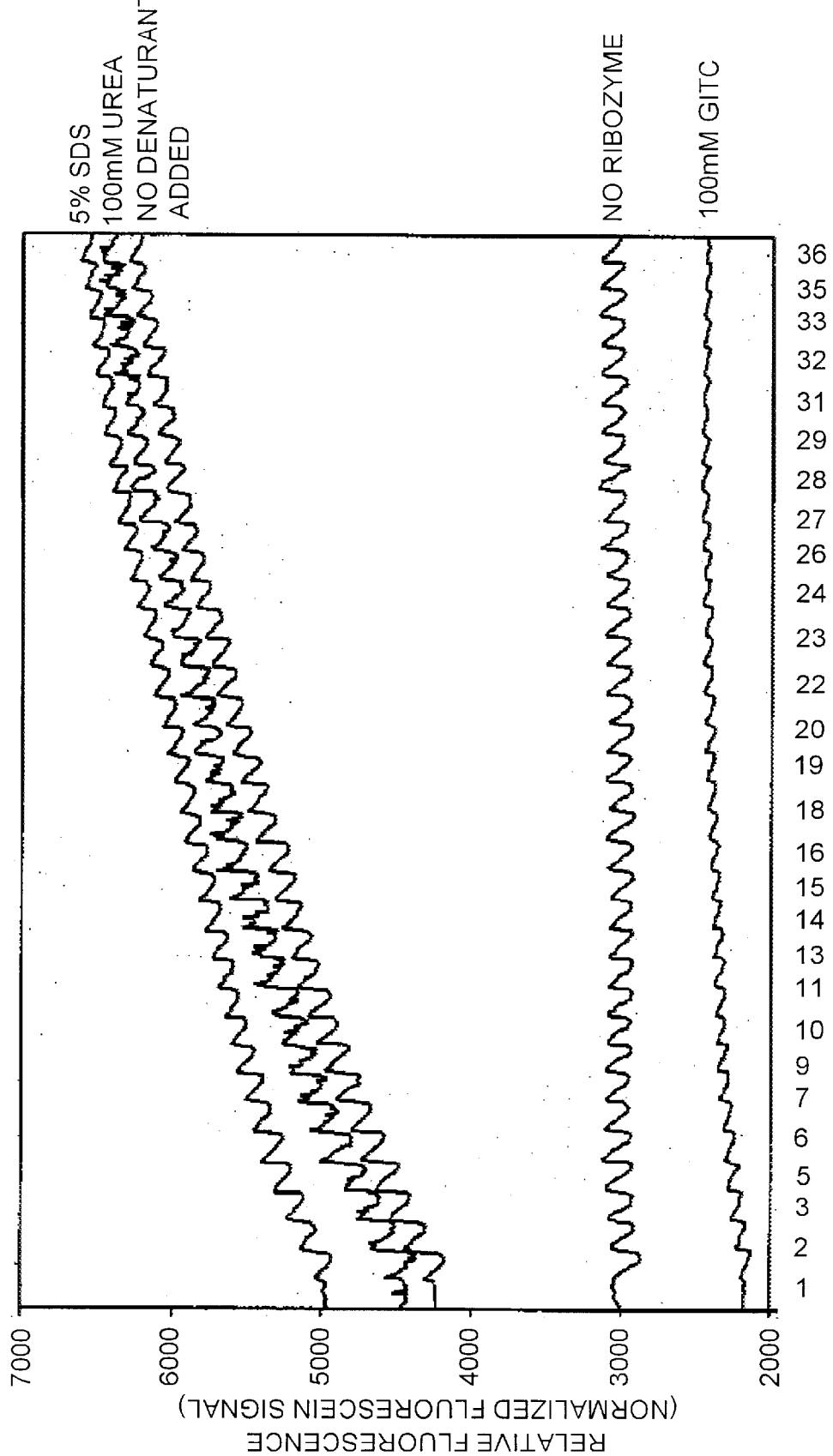
FIG. 21 shows relative fluorescence as a function of time indicating ribozyme ligation activity in the presence of 5% SDS 100 mM urea or without additions.

Each measurement is evident by a small peak: due to photobleaching, the signal drops during the measuring period and recovers during the dark interval. The results are shown in FIG. 21.

Reaction conditions: 1 mM SunY and 1 M 5'-fluorescein-labeled PI BS and 5 μM 5'-CY-5-labeled PIP were incubated in the ABI Prism 7700 for real time monitoring. Incubation at 45° C. was performed for 180 mins. with data collection in 5 minute intervals. Change of the relative fluorescence of the reporter dye fluorescein is shown. For further analysis, 10 μl aliquots of the samples were analyzed by denaturing polyacrylamide gel electrophoresis (shown in FIG. 19). The comparison shows that GITC quenches the fluorescein signal, but does not inhibit the ribozyme reaction.

Figure 20:
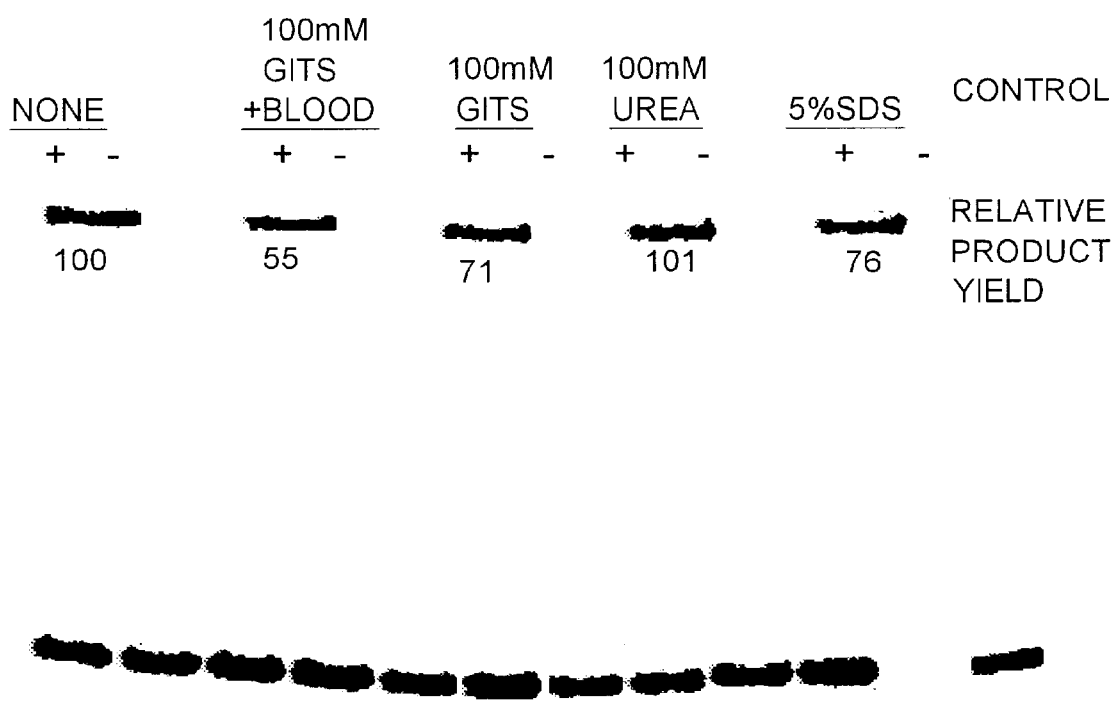
FIG. 20 shows the effect of denaturating PAGE after FRET monitoring.

The results are shown in FIG. 20 which shows also the effect of denaturants on reaction rate and detection.

In the absence of ribozyme, there is no change of the FRET signal. In the presence of ribozyme, without further additives, the signal changes from an initial value "4.2" to the final value "6.2".

Very similar changes were observed, if 200 mM urea or 5% SDS have been added, indicating that these additives do not change significantly the reaction rate nor the detectable signal.

Although 100 mM guanidinium isothiocyanate (GITC) does not inhibit the ribozyme reaction (FIG. 12), it is impossible to include GITC if fluorescein is used as reporter dye since GITC is a very strong quencher for fluorescein. However the effect of GITC is specific to the dye since no quenching was observed with other fluorochromes like CY-5 (data now shown).

Example 12

I. Production of Target Dependent Ribozyme Proto-nucleozymes from a Random Sequence In vitro evolution was used to prepare proto-nucleozymes which are catalytically active only in the presence of a co-factor.

The selection scheme is similar to that employed by Bartel and Szotstak (Science, 261:1411–1418 (1993)). A random sequence RNA pool N90) begins with a 5' triphosphate. The pool is captured on an affinity matrix complementary to the 3' end of the pool and mixed with a RNA substrate tagged with a DNA sequence. Following ligation, the RNA can be eluted from the column, reverse-transcribed via a cDNA primer, and PCR-amplified via a primer that is complementary to the newly ligated DNA tag. A nested PCR reaction using an internal primer generates a template that can again be transcribed to regenerate selected ligases. This cycle can be used for selection of the fastest and most active ligases.

The schematic pool of RNA sequences on which selection is carried out is shown in FIG. 22, together with the sequence of its 3' tail and its complementary cDNA primer.

After several rounds of selection the pool was cloned and individual clones were assayed, for activity and dependence on co-factor sequence.

Figure 23:
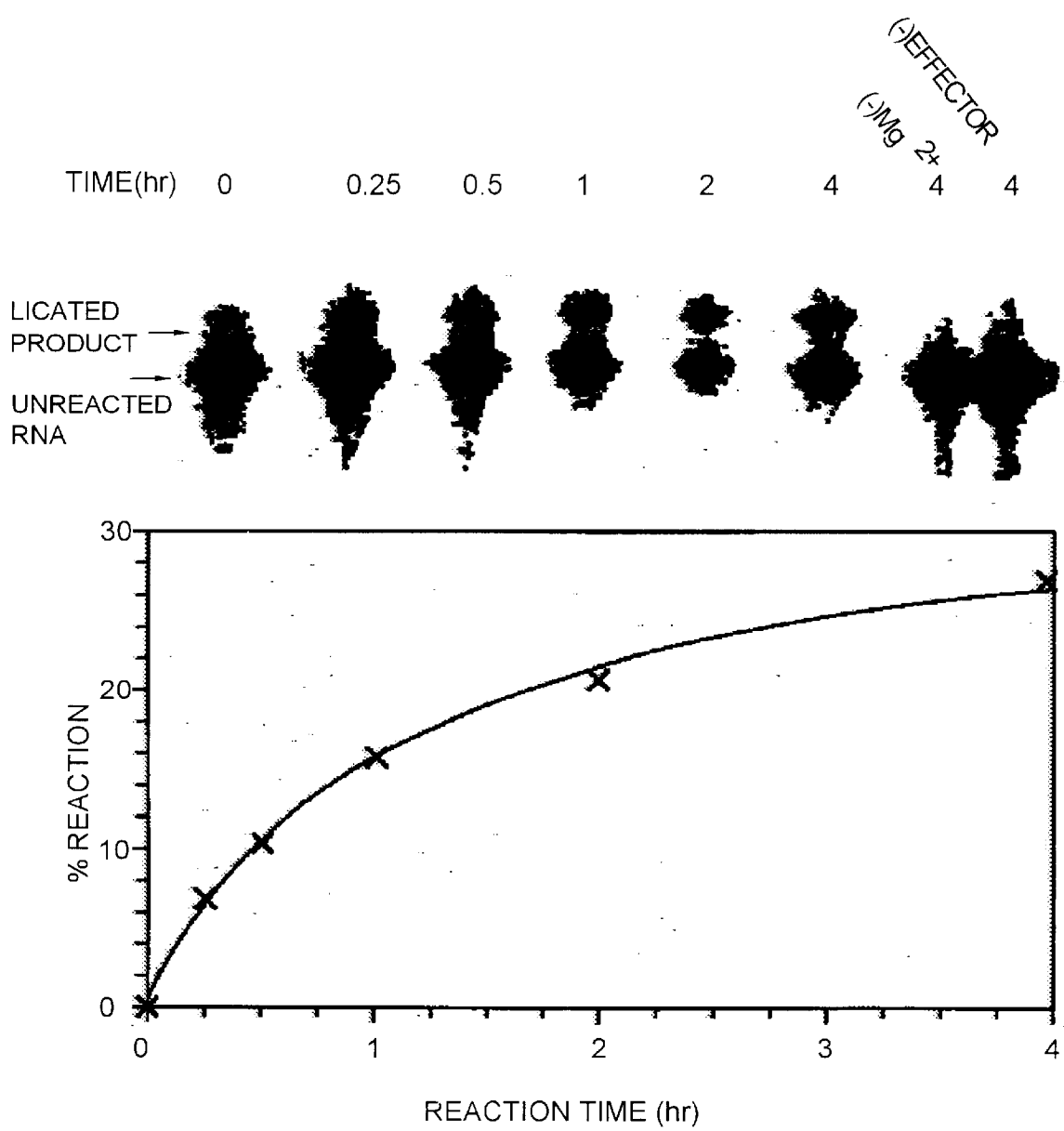
FIG. 23 shows the ligation activity of proto-nucleotides which is co-factor (termed also "effector") dependent.
Figure 24:
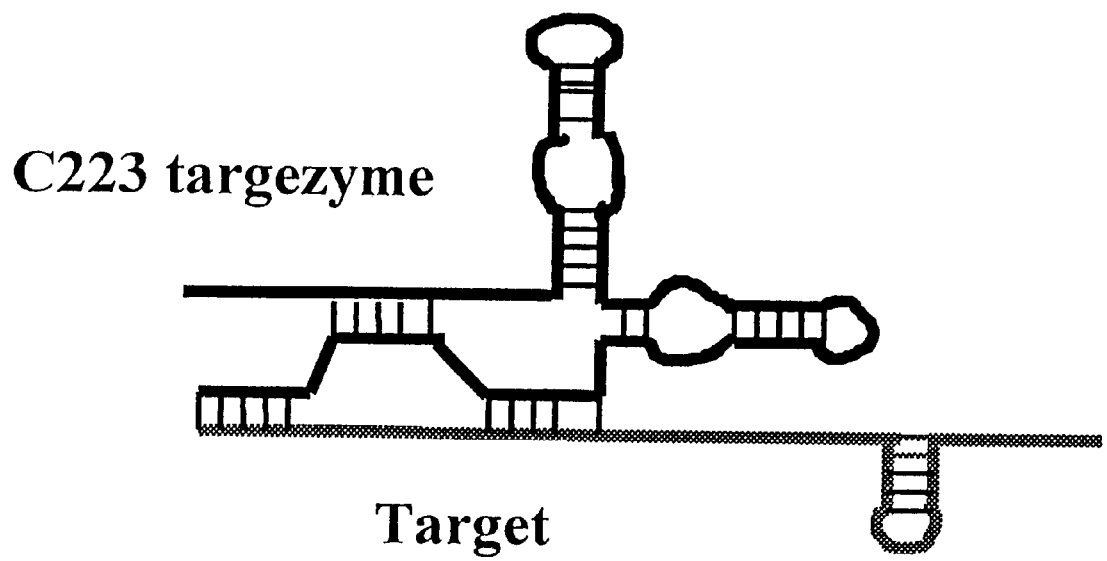
FIG. 24 shows a scheme of the bipartite C223 ribozyme.

The major class of selected ligases can efficiently catalyze the addition of the mixed labeled RNA-DNA substrate to themselves. A time course was carried out under standard assay conditions, and ligation products were separated from unligated ribozymes by separation on a denaturing PAA gel. In the absence of either $Mg^{+2}$ or the co-factor, which was a specific nucleic acid sequence, no reaction was observed. The relative amount of radioactive label in ligated and unligated ribozymes was determined using a Phosphoimager, background in the absence of co-factor was subtracted from these values, and the extent of reaction was plotted as a function of time. Initial rates and the fall extent of the reactions were determined using standard curve-fitting procedures, and are shown in FIG. 23. As can be seen in the absence of co-factor or $Mg^{+2}$ no ligated products was produced.

The clones were further examined for specificity. A series of DNA or RNA nucleotide sequence co-factors was synthesized and their abilities to activate the proto-nucleozymes were determined. Values were calculated as described above '-' indicates that no activity could be measured relative to background. Experiments carried out in duplicate or triplicate indicated that the relative activities of "active" (e.g. lines (1) and (9)) and "inactive" (e.g. lines (6) and (10)) co-factors are consistent between experiments.

The results are shown in Table 4.

TABLE 4

Specificity of the co-factor-Dependent Ribozyme

| Terminal guide sequence of ribozymes | | | | relative activity (ribozyme) |
|---|---|---|---|---|
| . . . | | GG UGC CUC GUG AUG UCC AGU CGC ACG 3' (SEQ ID NO: 39) | | |
| | Co-factor sequence | | Type | |
| 1 | (SEQ ID NO:12) | GAG CAC TAC AGG TCA GCG | 5' wild type | 1.0 |
| 2 | (SEQ ID NO:13) | G GAG CAC TAC AGG TCA GCG | 5' Extended (+1) | 0.09 |
| 3 | (SEQ ID NO:14) | AG CAC TAC AGG TCA GCG T | 5' receded (−1) | — |

TABLE 4-continued

Specificity of the co-factor-Dependent Ribozyme

| | | | | |
|---|---|---|---|---|
| 4 | (SEQ ID NO:15) | AAG CAC TAC AGG TCA GCG | 5' C:A mismatch | 0.08 |
| 5 | (SEQ ID NO:15) | AAG CAC TAC AGG TCA GCG | 5' fully complementary | 1.1 |
| 6 | (SEQ ID NO:16) | GAG CAC TAC AGG TCA GCG | 5' dideoxy terminal | — |
| 7 | (SEQ ID NO:17) | GAG CAC UAC AGG UCA GCG | 5' wild type RNA | 0.72 |
| 8 | (SEQ ID NO:18) | GAG CAT TAC AGG TCA GCG | 5' G:T wobble | 1.0 |
| 9 | (SEQ ID NO:19) | GAG CAC TAC AGG | 5' wild type (12) | 0.44 |
| 10 | (SEQ ID NO:23) | GAA CAC TAC AGG | 5' C:A mismatch | — |

TGS transition mutant ribozyme

| Terminal guide sequence of ribozymes | . . . | GG UGC CCU ACA GCA CUU GAC UAU | 3' (SEQ ID NO: 20) | relative activity (ribozyme) |
|---|---|---|---|---|
| | Co-factor sequence | | Type | |
| 11 | (SEQ ID NO:21) | GAG CAC TAC AGG TCA GCG | 5' wild type | — |
| 12 | (SEQ ID NO:22) | GGA TGT CGT GAA CTG ATA | 5' fully complementary | 1.3 |

A variety of potential co-factors were synthesized and assayed for their ability to enhance ligase activity; the results of these experiments are shown in Table 3. Oligonucleotide co-factors that extended complementary towards the 5' end of the RNA or that receded towards the 3 end showed little or no activation relative to no effector controls (Table III, lines (2) and (3)). These results seemed to indicate that the position of the co-factor was essential for activity, and that the 3' end of the co-factor might play a role in activation. A co-factor was synthesized with a G to A substitution at the 3' terminus. The C:A mismatch was much less active than the fully complementary effector (line (4)). However, the loss of activity seen with the G to A change in the effector could be suppressed by a compensatory C to U change in the ribozyme (line(S)). These results seemed to indicate that the 3' end of the ribozyme was acting like a "terminal guide sequence" (TGS). The co-factor that terminated in a dideoxy nucleotide could not activate catalysis (line(6)). In contrast, an all-RNA co-factor activated catalysis nearly as well (relative activity=0.72; line (7)) as the original all-DNA effector. Taken together, these results emphasize that the ribozyme is capable of specific recognition of its specific oligonucleotide co-factor.

II. Activation in the Presence of Random Sequences

The experiment described in I above was repeated with a co-factor of 12 mer in the presence of a random sequence of 12 nucleotide, or in the presence of both the random sequence and the co-factor, either when both are at the same concentration (1.3 $\mu$M) or where the random sequence is at an excess (10:1).

The results are shown in FIG. 23. As can be seen a 12 mer co-factor was able to activate the proto-nucleozyme at several concentrations while the random sequence pool showed no such activation. Moreover, the random sequence pool, even in excess concentration does not interfere with the ability of the correct co-factor to activate the proto-nucleozyme. These results show the specificity of the proto-nucleozyme of the invention to its specific co-factor and demonstrate that the presence of other sequences does not interfere with this specificity.

What is claimed is:

1. A proto-nucleozyme of a nucleozyme, the nucleozyme having a catalytic activity under a set of conditions, the proto-nucleozyme differing from the nucleozyme in a sequence of one or more nucleotides that is present in the nucleozyme and is absent in the proto-nucleozyme or replaced in the proto-nucleozyme by a different sequence of nucleotides, the proto-nucleozyme not having the catalytic activity of the nucleozyme under said set of conditions, and the proto-nucleozyme having said catalytic activity in the presence of a non-nucleic acid co-factor, wherein the non-nucleic acid cofactor is not a nucleotide, nucleoside, or a derivative thereof, and wherein the non-nucleic acid cofactor is a molecule which chemically interacts with nucleotides to provide the component missing in the proto-nucleozyme to convert the proto-nucleozyme into-a catalytically active nucleozyme.

2. A proto-nucleozyme according to claim 1, wherein the nucleozyme is a ribozyme.

3. A proto-nucleozyme according to claim 1, being a product of in vitro evolution.

4. A proto-nucleozyme according to claim 1, wherein the non-nucleic acid co-factor is selected from the group consisting of: proteins, peptides, oligopeptides, antibiotics, carbohydrates and lipids.

5. A composition comprising a proto-nucleozyme according to claim 1 and a pharmaceutically acceptable carrier.

6. A composition according to claim 5, wherein said carrier comprises liposomes.

7. An in vitro evolution method for the production of a proto-nucleozyme of claim 1, the method comprising:
(a) preparing a panel of different nucleic acid molecules, at least part of the sequence in the molecules of the panel is a random or a partially random sequence, such that said part has a different sequence in different molecules of the panel;
(b) adding said co-factor to said panel and under conditions permitting said catalytic activity;
(c) separating between the nucleic acid molecule of said panel which feature said catalytic activity and such which do not obtain first selected panel of nucleic acid molecules which feature said catalytic activity;
(d) amplifying the nucleic acid molecules of said first selected panel;
(e) incubating said first selected panel with a reaction mixture, being devoid of said co-factor, under conditions permitting said catalytic activity;
(f) removing nucleic acid molecules which featured catalytic activity, thereby obtaining a second selected panel of nucleic acid molecules devoid of the removed nucleic acid molecules; and
(g) repeating steps (b)–(f) over a plurality of cycles, to obtain said proto-nucleozyme.

8. A method according to claim 7, wherein said cycles are repeated 10–100 times.

9. A method according to claim 7, wherein the molecules of the panel of nucleic acid molecules in step (a) have a sequence which is derived from a known nucleozyme sequence with some proportion of the nucleotides being replaced by other nucleotides.

10. A method according to claim 8, wherein said some proportion is about 1–30%.

11. A method according to claim 9, comprising at least one amended cycle, wherein the amplification step of the molecules of the selected panel comprises also replacing a small proportion of the nucleotides in the molecules of said selected panel.

12. A method according to claim 11, comprising a plurality of such amended cycles.

13. An in vitro evolution method for the production of the proto-nucleozyme of claim 1, which nucleozyme together with a co-factor from a catalytic complex having a catalytic activity imparted by a functional sequence of said proto-nucleozyme, the method comprising:
(a) preparing a mixture of different oligonucleotide candidates for evolving to said proto-nucleozyme each of which comprises a variable sequence being a candidate for evolving in said functional sequence and a tag sequence, each of the two sequences being different than corresponding sequences of different oligonucleotides in the mixture, the variable sequence and the tag sequence being linked by at least one cleavable sequence;
(b) processing the mixture through positive and negative selection steps, each step optionally followed by an oligonucleotide amplification step, there being at least one positive selection step and at least one negative selection step, these steps comprising:
(ba) a positive selection step comprising applying said specific co-factor and separating between the oligonucleotides which have and those which do not have the catalytic activity to obtain a first selected mixture comprising a first group of oligonucleotides featuring catalytic activity in the presence of the co-factor;
(bb) an amplification step comprising amplifying said first group of oligonucleotides in said first selected mixture to produce a plurality of copies of each of said first group of oligonucleotides to obtain a first amplified mixture;
(bc) a negative selection step comprising:
(bca) applying a reaction mixture devoid of the specific co-factor and separating between a second group of oligo-nucleotides which do not have the catalytic activity in the absence of the co-factor and a third group of oligo-nucleotides having the catalytic activity in the absence of the co-factor, to obtain a second selected mixture comprising said second group of oligonucleotides and a third selected mixture comprising said third group of oligonucleotides;
(bcb) amplifying said third group of oligonucleotides in said third selected mixture to produce a plurality of copies of each of said third group of oligonucleotides to obtain a second amplified mixture;
(bcc) cleaving the cleavable sequence of the oligonucleotides in the second amplified mixture, separating between the variable and the tab sequences and collecting the tag sequences;
(bcd) contacting the collected tag sequences with the second selected mixture under stringent conditions of hybridization and removing hybridized oligonucleotides from other oligonucleotides of the second mixture, thereby obtaining a fourth selected mixture of oligonucleotides essentially devoid of oligonucleotides which have catalytic activity in the absence of the co-factor;
where said positive selected step precedes said negative selection step, said positive selection step is applied on said mixture prepared in step (a) and said negative selection step is applied on said first amplified mixture; and where said negative selection step precedes said positive selection step, said negative selection step is applied on said mixture obtained in step (a) and said positive selection step is applied on said fourth mixture.

14. A proto-nucleozyme of a nucleozyme, the nucleozyme having a catalytic activity under a set of conditions, the proto-nucleozyme differing from the nucleozyme in a sequence of one or more nucleotides that is present in the nucleozyme and is absent in the proto-nucleozyme or is replaced in the proto-nucleozyme by another sequence of nucleotides, the proto-nucleozyme not having the catalytic activity of the nucleozyme under said set of conditions, and having the catalytic activity of the nucleozyme in the presence of a co-factor that is a nucleic acid molecule or a nucleic acid sequence within a nucleic acid molecule, from a heterologous source.

* * * * *

SEQUENCE LISTING

<160> NUMBER OF SEQ ID NOS: 39

<210> SEQ ID NO 1
<211> LENGTH: 23
<212> TYPE: RNA
<213> ORGANISM: Humanus

<400> SEQUENCE: 1
ggcuuagaga agaaauucuu uaa    23

<210> SEQ ID NO 2
<211> LENGTH: 20
<212> TYPE: RNA
<213> ORGANISM: Humanus

<400> SEQUENCE: 2
agcuauagac aaggcaaucc    20

<210> SEQ ID NO 3
<211> LENGTH: 10
<212> TYPE: RNA
<213> ORGANISM: Humanus

<400> SEQUENCE: 3
auucuccacc                                                              10

<210> SEQ ID NO 4
<211> LENGTH: 30
<212> TYPE: RNA
<213> ORGANISM: Humanus

<400> SEQUENCE: 4
aaagccaaua ggcaguagcg aaagcugcgg                                        30

<210> SEQ ID NO 5
<211> LENGTH: 14
<212> TYPE: RNA
<213> ORGANISM: Humanus

<400> SEQUENCE: 5
ggggugaccc gauc                                                         14

<210> SEQ ID NO 6
<211> LENGTH: 10
<212> TYPE: RNA
<213> ORGANISM: Humanus

<400> SEQUENCE: 6
auucuccacc                                                              10

<210> SEQ ID NO 7
<211> LENGTH: 67
<212> TYPE: DNA
<213> ORGANISM: Humanus

<400> SEQUENCE: 7
ctttcggtta agggagagtc tatgtgatat cagctagttg gtggggtaaa ggcctaccaa       60
ggctatg                                                                 67

<210> SEQ ID NO 8
<211> LENGTH: 67
<212> TYPE: DNA
<213> ORGANISM: Humanus

<400> SEQUENCE: 8
ctttcggttg aggaagagtt tatgcgatat cagcttgttg gtggggtaaa agcccaccaa       60
ggcgatg                                                                 67

<210> SEQ ID NO 9
<211> LENGTH: 67
<212> TYPE: DNA
<213> ORGANISM: Humanus

<400> SEQUENCE: 9
ctttcggtta agggagagtc tatgggatat cagcttgttg gtggggtaat ggcctaccaa       60
ggttttg                                                                 67

<210> SEQ ID NO 10
<211> LENGTH: 67

-continued

```
<212> TYPE: DNA
<213> ORGANISM: Humanus

<400> SEQUENCE: 10
cttgcgctat ccgagcggcc gatatctgat tagctggttg gcggggtaaa ggcccaccaa      60
ggcgacg                                                                67

<210> SEQ ID NO 11
<211> LENGTH: 67
<212> TYPE: DNA
<213> ORGANISM: Humanus

<400> SEQUENCE: 11
ctcttgccat cggatgtgcc cagatgggat tagctagtag gtggggtaac ggctcaccta      60
ggcgacg                                                                67

<210> SEQ ID NO 12
<211> LENGTH: 18
<212> TYPE: DNA
<213> ORGANISM: Humanus

<400> SEQUENCE: 12
gcgactggac atcacgag                                                    18

<210> SEQ ID NO 13
<211> LENGTH: 19
<212> TYPE: DNA
<213> ORGANISM: Humanus

<400> SEQUENCE: 13
gcgactggac atcacgagg                                                   19

<210> SEQ ID NO 14
<211> LENGTH: 18
<212> TYPE: DNA
<213> ORGANISM: Humanus

<400> SEQUENCE: 14
tgcgactgga catcacga                                                    18

<210> SEQ ID NO 15
<211> LENGTH: 18
<212> TYPE: DNA
<213> ORGANISM: Humanus

<400> SEQUENCE: 15
gcgactggac atcacgaa                                                    18

<210> SEQ ID NO 16
<211> LENGTH: 18
<212> TYPE: DNA
<213> ORGANISM: Humanus

<400> SEQUENCE: 16
gcgactggac atcacgag                                                    18

<210> SEQ ID NO 17
<211> LENGTH: 18
<212> TYPE: RNA
<213> ORGANISM: Humanus

<400> SEQUENCE: 17
```

```
gcgacuggac aucacgag                                              18

<210> SEQ ID NO 18
<211> LENGTH: 18
<212> TYPE: DNA
<213> ORGANISM: Humanus

<400> SEQUENCE: 18
gcgactggac attacgag                                              18

<210> SEQ ID NO 19
<211> LENGTH: 12
<212> TYPE: DNA
<213> ORGANISM: Humanus

<400> SEQUENCE: 19
ggacatcacg ag                                                    12

<210> SEQ ID NO 20
<211> LENGTH: 23
<212> TYPE: RNA
<213> ORGANISM: Humanus

<400> SEQUENCE: 20
ggugcccuac agcacuugac uau                                        23

<210> SEQ ID NO 21
<211> LENGTH: 18
<212> TYPE: DNA
<213> ORGANISM: Humanus

<400> SEQUENCE: 21
gcgactggac atcacgag                                              18

<210> SEQ ID NO 22
<211> LENGTH: 18
<212> TYPE: DNA
<213> ORGANISM: Humanus

<400> SEQUENCE: 22
atagtcaagt gctgtagg                                              18

<210> SEQ ID NO 23
<211> LENGTH: 12
<212> TYPE: DNA
<213> ORGANISM: Humanus

<400> SEQUENCE: 23
ggacatcaca ag                                                    12

<210> SEQ ID NO 24
<211> LENGTH: 123
<212> TYPE: RNA
<213> ORGANISM: Humanus

<400> SEQUENCE: 24
gaaaaucugc cuaaacgggg aaacucucag cgagacaauc ccgugcuaaa ucagcaauag    60
cuguaaaugc cuaacgacua cucgguagac aacucuaaga guugaaggua uagucuaaac   120
ugc                                                                 123

<210> SEQ ID NO 25
<211> LENGTH: 26
```

<212> TYPE: RNA
<213> ORGANISM: Humanus

<400> SEQUENCE: 25
ggagaaugau ggugacaugc aggauc                                    26

<210> SEQ ID NO 26
<211> LENGTH: 24
<212> TYPE: RNA
<213> ORGANISM: Humanus

<400> SEQUENCE: 26
ggagaauggg ugacgugcag gauc                                      24

<210> SEQ ID NO 27
<211> LENGTH: 125
<212> TYPE: RNA
<213> ORGANISM: Humanus

<400> SEQUENCE: 27
gaaaaucugc cuaaacgggg aaacucucag ugagacaauc ccgugcuaaa ucagcaauag    60
cuguaaaugc cuaacgacua cucgguagac aacucuaaga guugaaggua uagucuaaac   120
ugcau                                                              125

<210> SEQ ID NO 28
<211> LENGTH: 149
<212> TYPE: RNA
<213> ORGANISM: Humanus

<400> SEQUENCE: 28
gaaaaucugc cuaaacgggg aaacucucag ugagacaauc ccgugcuaaa ucagcaauag    60
cuguaaaugc cuaacgacua cucgguagac aacucuaaga guugaaggua uagucuaauu   120
cuccacccug cauggugaca ugcaggauc                                    149

<210> SEQ ID NO 29
<211> LENGTH: 21
<212> TYPE: RNA
<213> ORGANISM: Humanus

<400> SEQUENCE: 29
ggauaacuac auaucggagg g                                            21

<210> SEQ ID NO 30
<211> LENGTH: 59
<212> TYPE: RNA
<213> ORGANISM: Humanus

<400> SEQUENCE: 30
gaaaaucugc cuaaacgggg aaacucucac ugagacaauc ccgugcuaaa ucagcaaua     59

<210> SEQ ID NO 31
<211> LENGTH: 36
<212> TYPE: RNA
<213> ORGANISM: Humanus

<400> SEQUENCE: 31
gcuguaaaug ccuaacgacu acacgguaga caacuc                            36

<210> SEQ ID NO 32
<211> LENGTH: 43
<212> TYPE: RNA

```
<213> ORGANISM: Humanus

<400> SEQUENCE: 32
gaguugaagg uauagucuaa acugcauggu gacaugcagg auc              43

<210> SEQ ID NO 33
<211> LENGTH: 59
<212> TYPE: RNA
<213> ORGANISM: Humanus

<400> SEQUENCE: 33
gaaaacgccc auaaaccggg aaacucucac ugagacaauc cgguacuuaa ucaccaaua    59

<210> SEQ ID NO 34
<211> LENGTH: 38
<212> TYPE: RNA
<213> ORGANISM: Humanus

<400> SEQUENCE: 34
ggugcuagcg uuaaucggau uuauugggcg uaaaggua                    38

<210> SEQ ID NO 35
<211> LENGTH: 52
<212> TYPE: RNA
<213> ORGANISM: Humanus

<400> SEQUENCE: 35
accuuuaaag guaaauccaa auucuccacc cugcauggug acaugcagga uc      52

<210> SEQ ID NO 36
<211> LENGTH: 33
<212> TYPE: RNA
<213> ORGANISM: Humanus

<400> SEQUENCE: 36
gaggcuggag uagaauauuu acccuccggc cuc                         33

<210> SEQ ID NO 37
<211> LENGTH: 28
<212> TYPE: RNA
<213> ORGANISM: Humanus

<400> SEQUENCE: 37
agcacuggac uucgguccag ugcucgug                               28

<210> SEQ ID NO 38
<211> LENGTH: 18
<212> TYPE: DNA
<213> ORGANISM: Humanus

<400> SEQUENCE: 38
cucgugaugu ccagucgc                                          18

<210> SEQ ID NO 39
<211> LENGTH: 26
<212> TYPE: DNA
<213> ORGANISM: Humanus

<400> SEQUENCE: 39
ggugccucgu gauguccagu cgcacg                                 26
```